(12) United States Patent
Kimrey, Jr.

(10) Patent No.: US 9,179,505 B2
(45) Date of Patent: Nov. 3, 2015

(54) OPTIMIZED MOTION AND LOCATION OF INTENSE MICROWAVE FIELDS WITHIN A HEATING SYSTEM

(71) Applicant: Microwave Materials Technologies, Inc., Knoxville, TN (US)

(72) Inventor: Harold Dail Kimrey, Jr., Knoxville, TN (US)

(73) Assignee: Microwave Materials Technologies, Inc., Knoxville, TN (US)

(*) Notice: Subject to any disclaimer, the term of this patent is extended or adjusted under 35 U.S.C. 154(b) by 294 days.

(21) Appl. No.: 13/799,684

(22) Filed: Mar. 13, 2013

(65) Prior Publication Data

US 2013/0240507 A1    Sep. 19, 2013

Related U.S. Application Data

(60) Provisional application No. 61/610,756, filed on Mar. 14, 2012, provisional application No. 61/610,708, filed on Mar. 14, 2012, provisional application No. 61/610,729, filed on Mar. 14, 2012, provisional (Continued)

(51) Int. Cl.
*H05B 6/68* (2006.01)
*H05B 6/80* (2006.01)
(Continued)

(52) U.S. Cl.
CPC ............ *H05B 6/68* (2013.01); *H01L 21/67201* (2013.01); *H05B 6/70* (2013.01); *H05B 6/78* (2013.01); *H05B 6/782* (2013.01); *H05B 6/80* (2013.01)

(58) Field of Classification Search
USPC ................... 219/697, 717, 746, 747; 333/230
See application file for complete search history.

(56) References Cited

U.S. PATENT DOCUMENTS

| | | | |
|---|---|---|---|
| 2,485,659 A | 10/1949 | Robertson | |
| 3,092,503 A | 6/1963 | Gray | |

(Continued)

FOREIGN PATENT DOCUMENTS

| | | | |
|---|---|---|---|
| JP | 2008-253202 A | 10/2008 | |
| JP | 2010-139217 A | 6/2010 | |

(Continued)

OTHER PUBLICATIONS

Craig B. Koskiniemi et al., Improvement of heating uniformity in packaged acidified vegetables pasteurized with a 915 MHz continuous microwave system, Journal of Food Engineering (105), Feb. 10, 2011, pp. 149-160, www.elsevier.com/locate/jfoodeng, Department of Food, Bioprocessing and Nutrition Sciences, North Carolina State University, Raleigh, NC, USA.

(Continued)

*Primary Examiner* — Jianying Atkisson
(74) *Attorney, Agent, or Firm* — Hovey Williams LLP

(57) ABSTRACT

A method and system for heating a plurality of articles is provided. The method includes discharging microwave energy into a microwave chamber and passing a plurality of articles through the heating zone. At least a portion of the microwave energy discharged into the heating zone may first be phase shifted using one or more phase shifting devices. One embodiment of a rotatable phase shifting device is also provided and includes an elongated fixed member disposed proximate a rotatable housing. The phase shifting device employed by the microwave heating system is configured such that the ratio of the article residence time in the heating zone to the phase shifting rate is at least about 4:1. Rotatable phase shifting devices, or variable phase short circuits, as described herein can also be used in other applications, such as, for example, as impedance or frequency tuning devices.

14 Claims, 18 Drawing Sheets

Related U.S. Application Data application No. 61/610,739, filed on Mar. 14, 2012, provisional application No. 61/610,745, filed on Mar. 14, 2012, provisional application No. 61/610,767, filed on Mar. 14, 2012, provisional application No. 61/610,776, filed on Mar. 14, 2012, provisional application No. 61/610,787, filed on Mar. 14, 2012, provisional application No. 61/610,794, filed on Mar. 14, 2012, provisional application No. 61/610,804, filed on Mar. 14, 2012, provisional application No. 61/610,821, filed on Mar. 14, 2012, provisional application No. 61/610,830, filed on Mar. 14, 2012.

(51) Int. Cl.
   *H05B 6/78* (2006.01)
   *H01L 21/67* (2006.01)
   *H05B 6/70* (2006.01)

(56) References Cited

U.S. PATENT DOCUMENTS

| | | |
|---|---|---|
| 3,261,140 A | 7/1966 | Long et al. |
| 3,398,251 A | 8/1968 | Jeppson et al. |
| 3,402,277 A | 9/1968 | Muller |
| 3,437,495 A | 4/1969 | Jeppson |
| 3,521,186 A | 7/1970 | Sharpe |
| 3,544,923 A | 12/1970 | Williams |
| 3,597,240 A | 8/1971 | Foltz |
| 3,718,082 A | 2/1973 | Lipoma |
| 3,820,549 A | 6/1974 | Flinchbaugh |
| 3,945,170 A | 3/1976 | Brown |
| 3,961,569 A | 6/1976 | Kenyon et al. |
| RE30,310 E | 6/1980 | Stenstrom |
| 4,282,887 A | 8/1981 | Sterzer |
| 4,301,347 A * | 11/1981 | Quine .......................... 219/747 |
| 4,332,091 A * | 6/1982 | Bensussan et al. ............. 34/265 |
| 4,336,434 A * | 6/1982 | Miller .......................... 219/747 |
| 4,393,088 A | 7/1983 | Matsusaka |
| 4,446,349 A * | 5/1984 | Smith .......................... 219/747 |
| 4,464,554 A * | 8/1984 | Bakanowski et al. ......... 219/748 |
| 4,518,618 A | 5/1985 | Hsia et al. |
| 4,608,261 A | 8/1986 | MacKenzie |
| 4,613,836 A * | 9/1986 | Evans .......................... 333/159 |
| 4,624,854 A | 11/1986 | Naumann et al. |
| 4,808,782 A | 2/1989 | Nakagawa et al. |
| 4,808,783 A | 2/1989 | Stenstrom |
| 4,839,142 A | 6/1989 | Charm |
| 4,839,485 A | 6/1989 | Koch et al. |
| 4,866,233 A | 9/1989 | Fritz |
| 4,874,917 A | 10/1989 | Weimer |
| 4,880,648 A | 11/1989 | Stamer |
| 4,999,471 A | 3/1991 | Guarneri et al. |
| 5,066,503 A | 11/1991 | Ruozi |
| 5,074,200 A | 12/1991 | Ruozi |
| 5,080,164 A | 1/1992 | Hermans |
| 5,101,084 A | 3/1992 | Atwell et al. |
| 5,160,819 A | 11/1992 | Ball et al. |
| 5,326,530 A | 7/1994 | Bridges |
| 5,410,283 A * | 4/1995 | Gooray et al. ................ 333/159 |
| 5,436,432 A | 7/1995 | Cyr |
| 5,546,849 A | 8/1996 | Shefet |
| 5,619,908 A | 4/1997 | Catelli et al. |
| 5,750,966 A | 5/1998 | Ruozi |
| 5,910,268 A | 6/1999 | Keefer |
| 6,153,868 A | 11/2000 | Marzat |
| 6,784,405 B2 | 8/2004 | Flugstad et al. |
| 7,119,313 B2 | 10/2006 | Tang et al. |
| 7,154,103 B2 | 12/2006 | Koenck et al. |
| 7,208,710 B2 | 4/2007 | Gregoire et al. |
| 7,230,218 B2 * | 6/2007 | Roussy ......................... 219/697 |
| 7,518,092 B2 | 4/2009 | Purta et al. |
| 7,993,603 B2 | 8/2011 | Amedeo et al. |
| 2005/0123435 A1 | 6/2005 | Cutler et al. |
| 2006/0151533 A1 | 7/2006 | Simunovic et al. |
| 2008/0299276 A1 | 12/2008 | Eubanks et al. |
| 2009/0092708 A1 | 4/2009 | Alvarado et al. |
| 2009/0236334 A1 | 9/2009 | Ben-Shmuel et al. |
| 2009/0283517 A1 | 11/2009 | Mackay et al. |
| 2010/0072194 A1 | 3/2010 | Mackay et al. |
| 2010/0126988 A1 | 5/2010 | Mackay et al. |
| 2010/0282741 A1 | 11/2010 | Van Daele et al. |
| 2011/0287151 A1 | 11/2011 | Simunovic et al. |
| 2012/0092091 A1 | 4/2012 | Kang |

FOREIGN PATENT DOCUMENTS

| | | |
|---|---|---|
| JP | 2010-166863 A | 8/2010 |
| KR | 10-0242633 B1 | 2/2000 |
| WO | 2007108674 | 9/2007 |

OTHER PUBLICATIONS

P. Kumar et al., Measurement of Dielectric Properties of Pumpable Food Materials under Static and Continuous Flow Conditions, JFS E: Food Engineering and Physical Properties, Journal of Food Science, vol. 72, Nr. 4, 2007, Institute of Food Technologists, pp. E177-E183.

Y. Wang et al., Sterilization of Foodstuffs Using Radio Frequency Heating, JFS E: Food Engineering and Physical Properties, Journal of Food Science, vol. 68, Nr. 2, 2003, Institute of Food Technologists, pp. 539-544.

Kunchalee Luechapattanaporn et al., Sterilization of Scrambled Eggs in Military Polymeric Trays by Radio Frequency Energy, JFS E: Food Engineering and Physical Properties, Journal of Food Science, vol. 70, Nr. 4, 2005, Institute of Food Technologists, pp. E288-E294.

Safety of Foods Processed Using Four Alternative Processing Technologies, Supported by USDA National Integrated Food Safety Initiative Project No. 2003-51110-02093, http://www.oardc.ohio-state.edu/sastry/USDA_project.htm, 4 pages.

FDA Proposes to Allow the Use of Alternative Temperature-Indicating Devices for Processing Low-Acid Canned Foods, FDS News Release, http://www.fda.gov/NewsEvents/Newsroom/PressAnnouncements/2007/ucm108867.htm, Mar. 13, 2007, 2 pages.

CFR—Code of Federal Regulations Title 21, http://www.accessdata.fda.gov/scripts/cdrh/cfdocs/cfCFR/CFRSearch.cfm?CFRPart=113, 2 pages.

CFR—Code of Federal Regulations Title 21, http://www.accessdata.fda.gov/scripts/cdrh/cfdocs/cfCFR/CFRSearch.cfm?CFRPart=11&showFR=1, 6 pages.

Juming Tang, Ph.D., Microwave (and RF) Heating in Food Processing Applications, Department of Biological Systems Engineering, Washington State University, Pullman, WA, 62 pages, Power Point Presentation.

Gustosi Italian Ready Meals, Screen shots of video found at http://www.gusto-si.it/engnew/technologia.html, Gustosi S.p.A., Frazione Baitoni, 10 pages.

Microwave sterilisation of foods: an industry—changing development, http://www.labint-online.com/featured-articles/microwave-sterilisation-of-foods-an-industry-changing-development/index.html, Pan Global, 2 pages.

International Search Report and Written Opinion of corresponding PCT Patent Application No. PCT/US2013/030844, filed Mar. 13, 2013, Dated Jun. 27, 2013; 33 Pages.

* cited by examiner

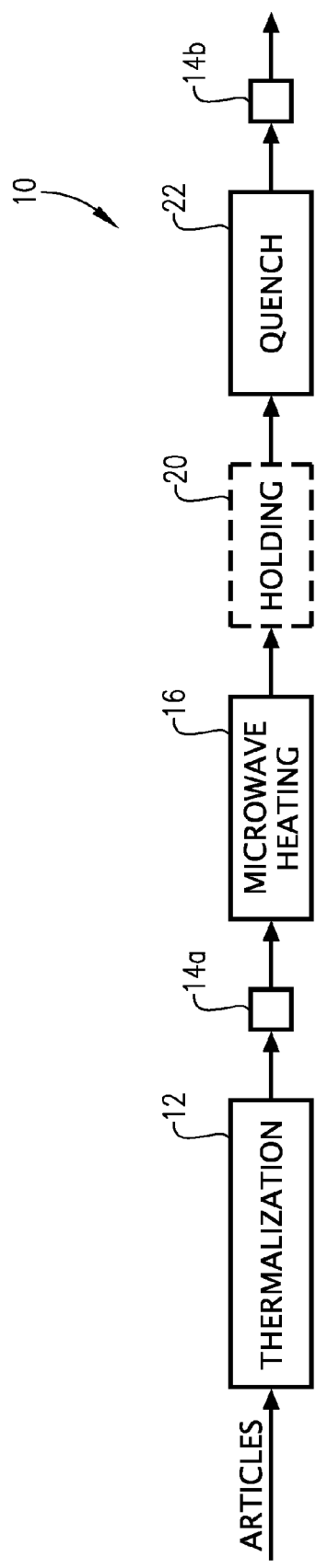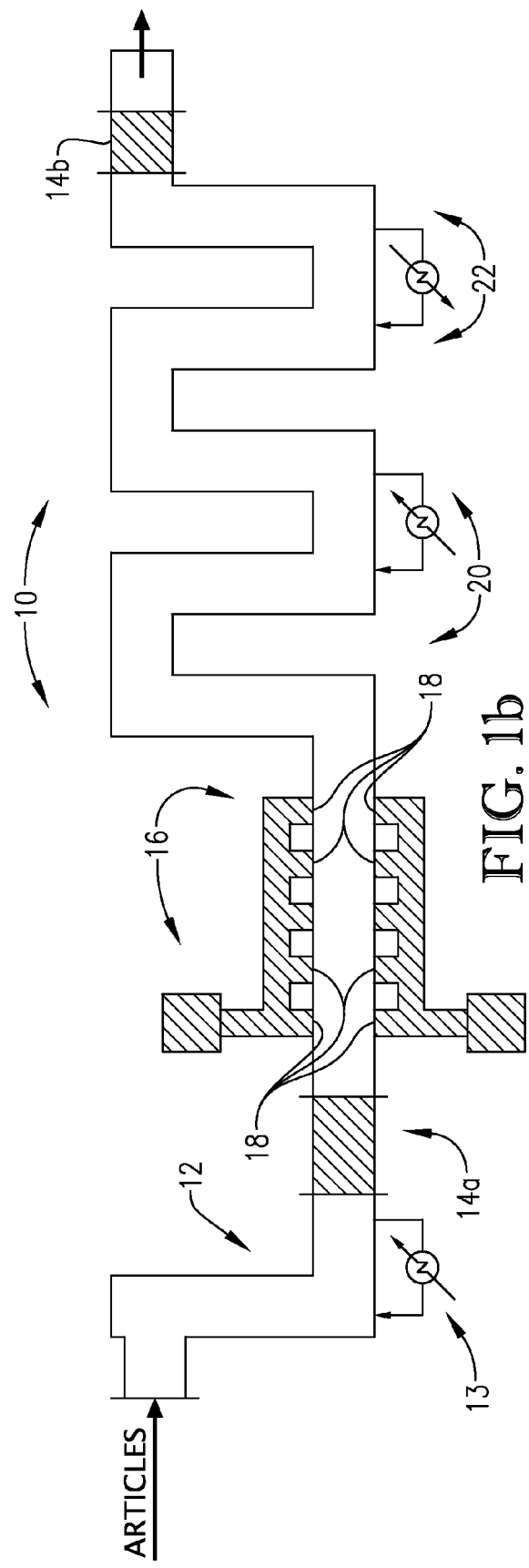

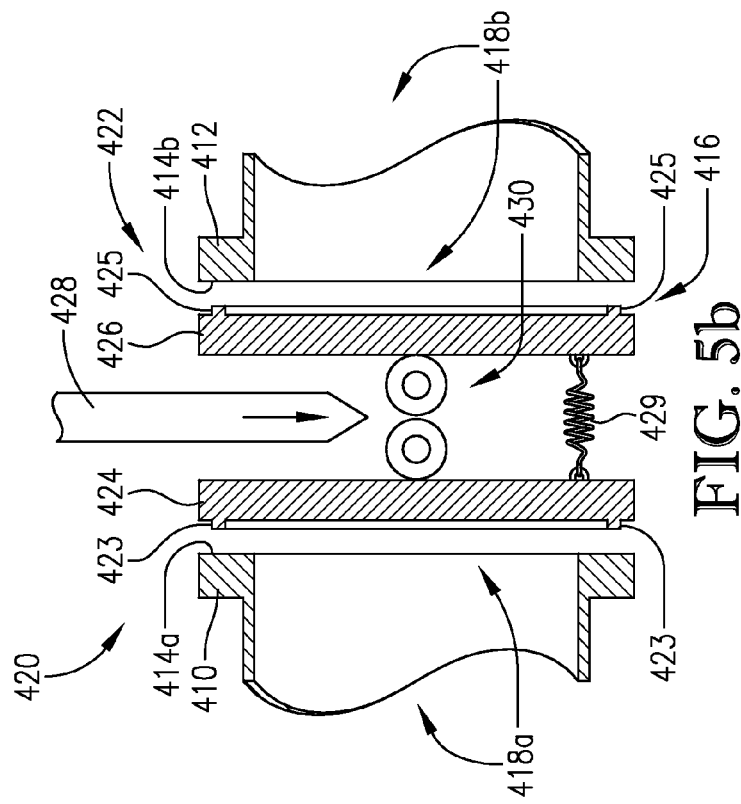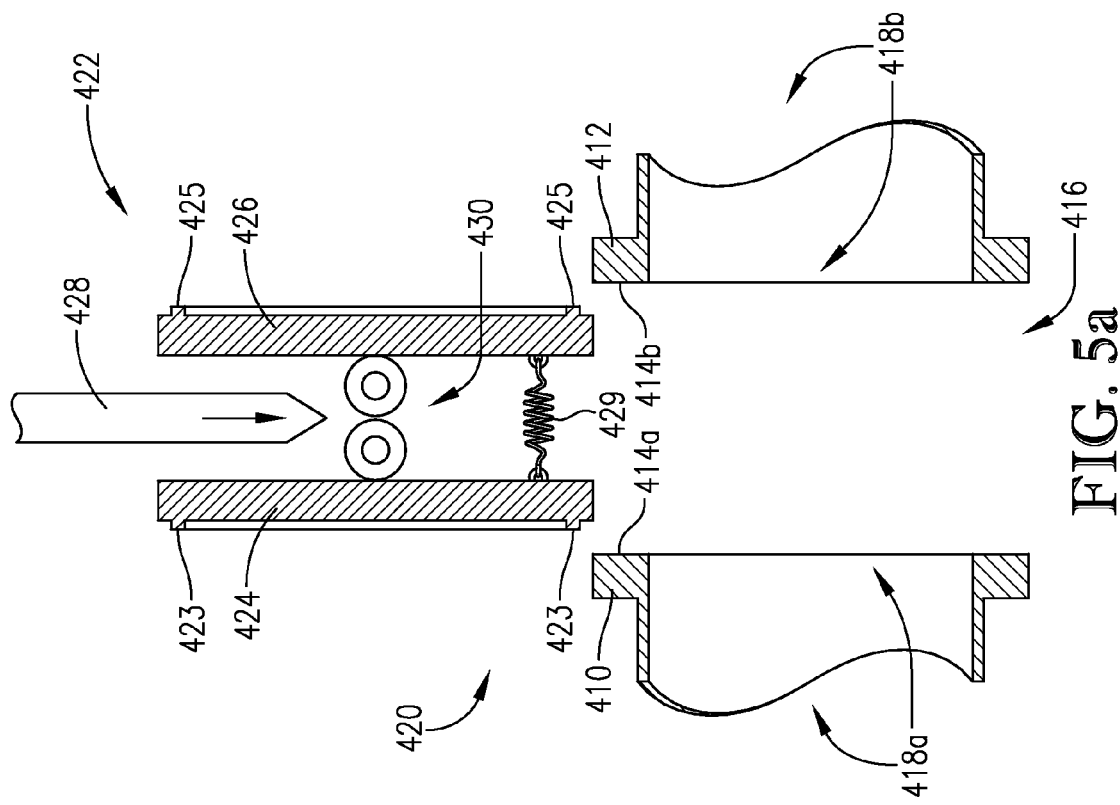

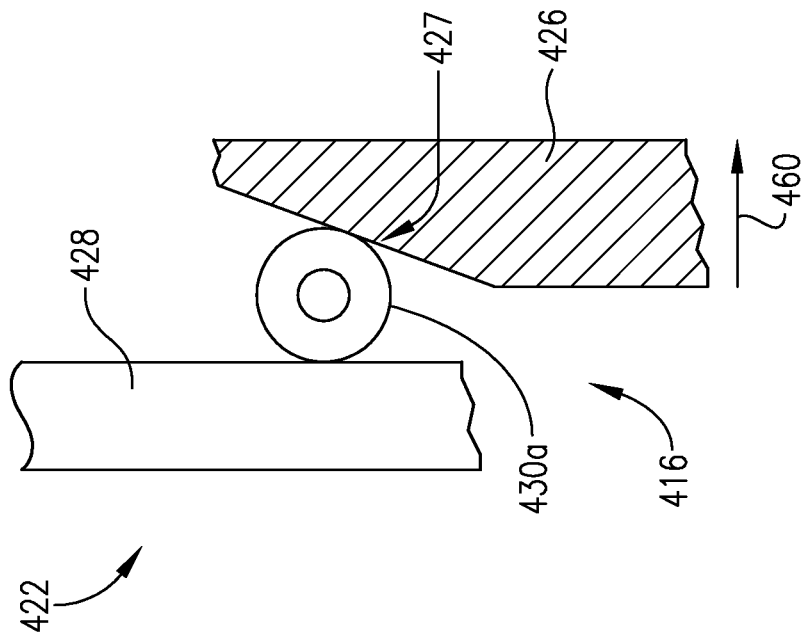
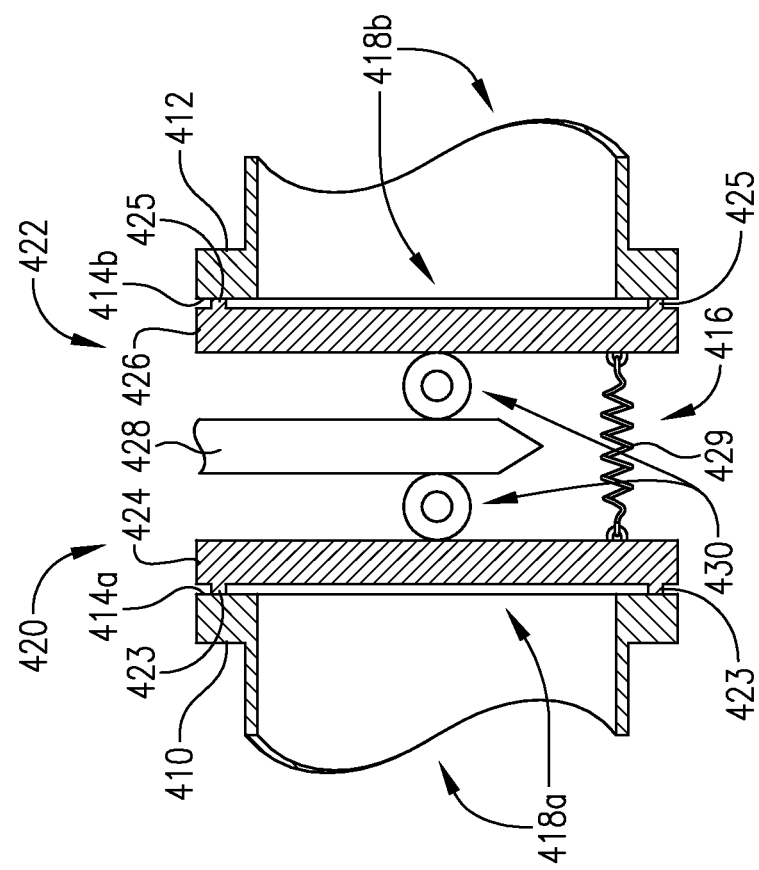

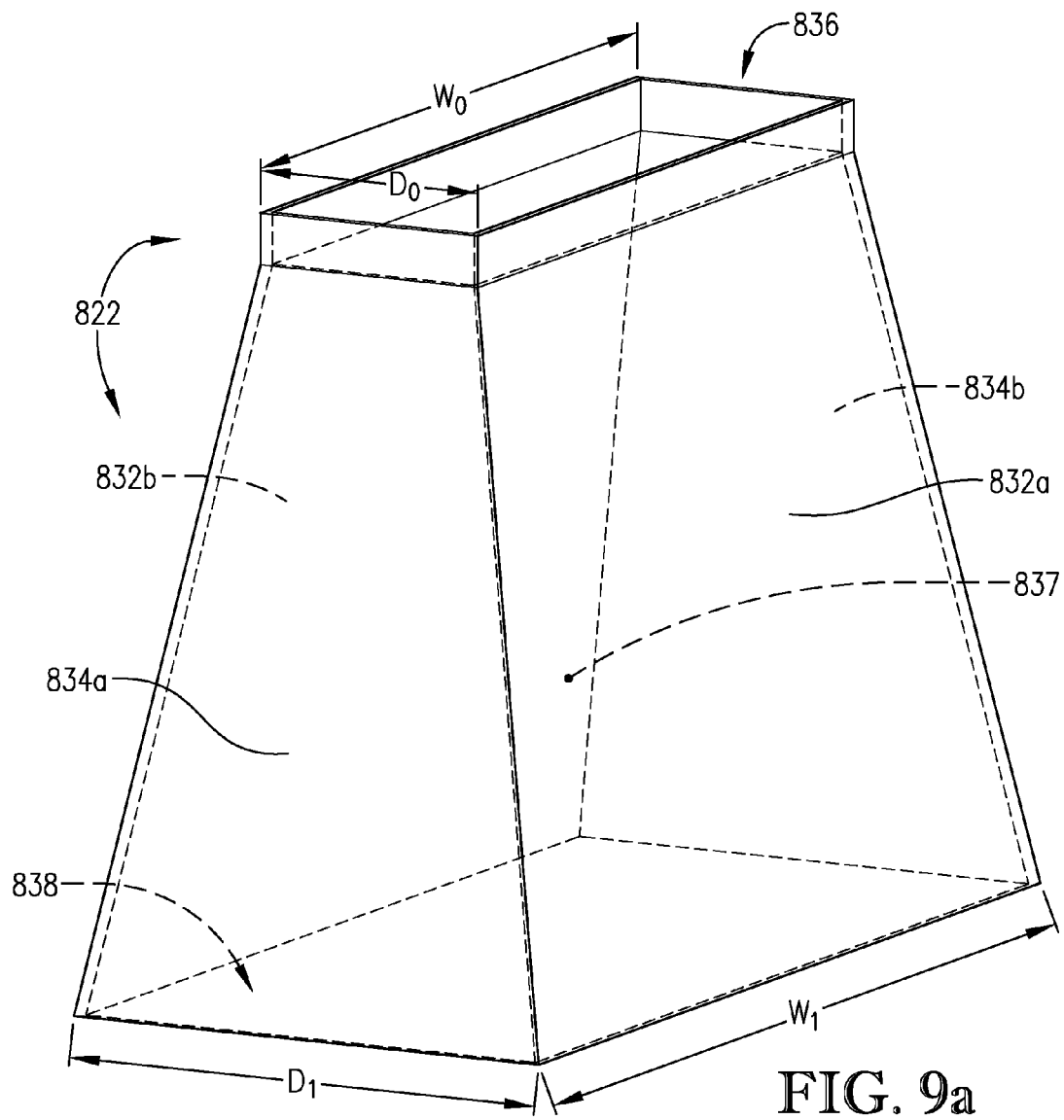
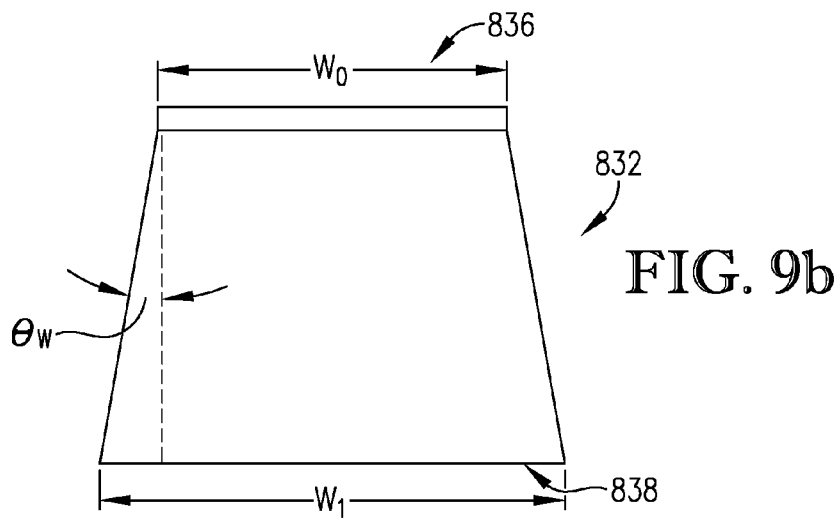
FIG. 9a
FIG. 9b

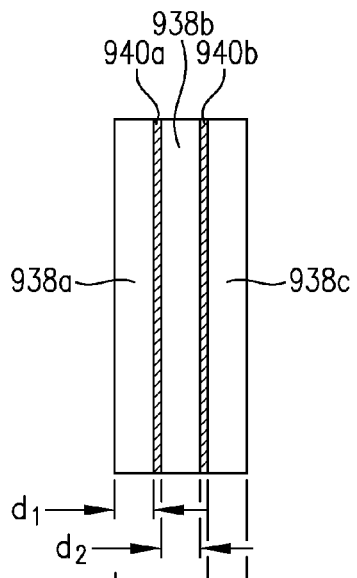
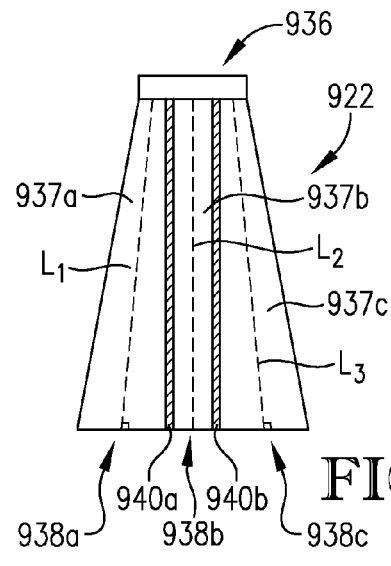
FIG. 10b
FIG. 10c
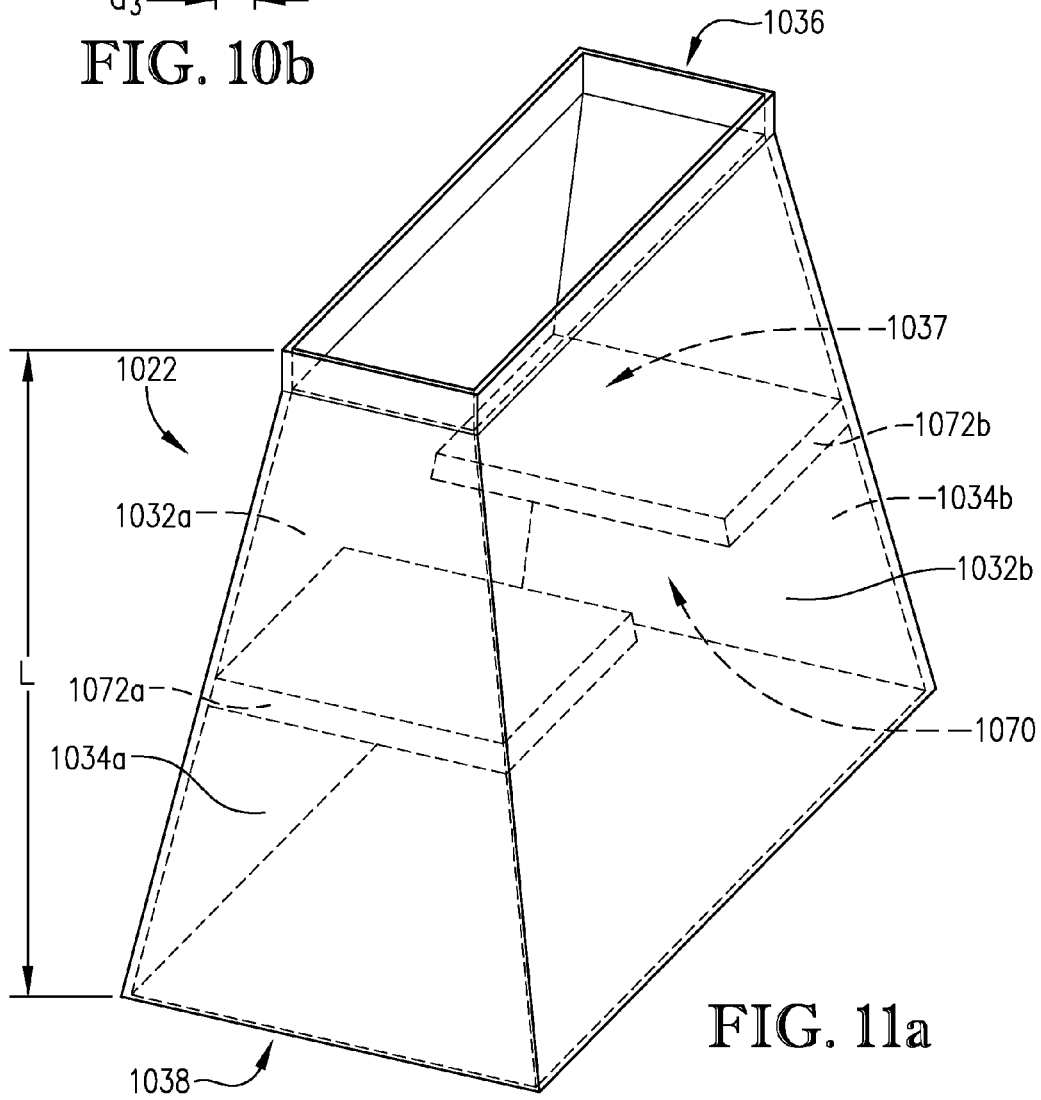
FIG. 11a

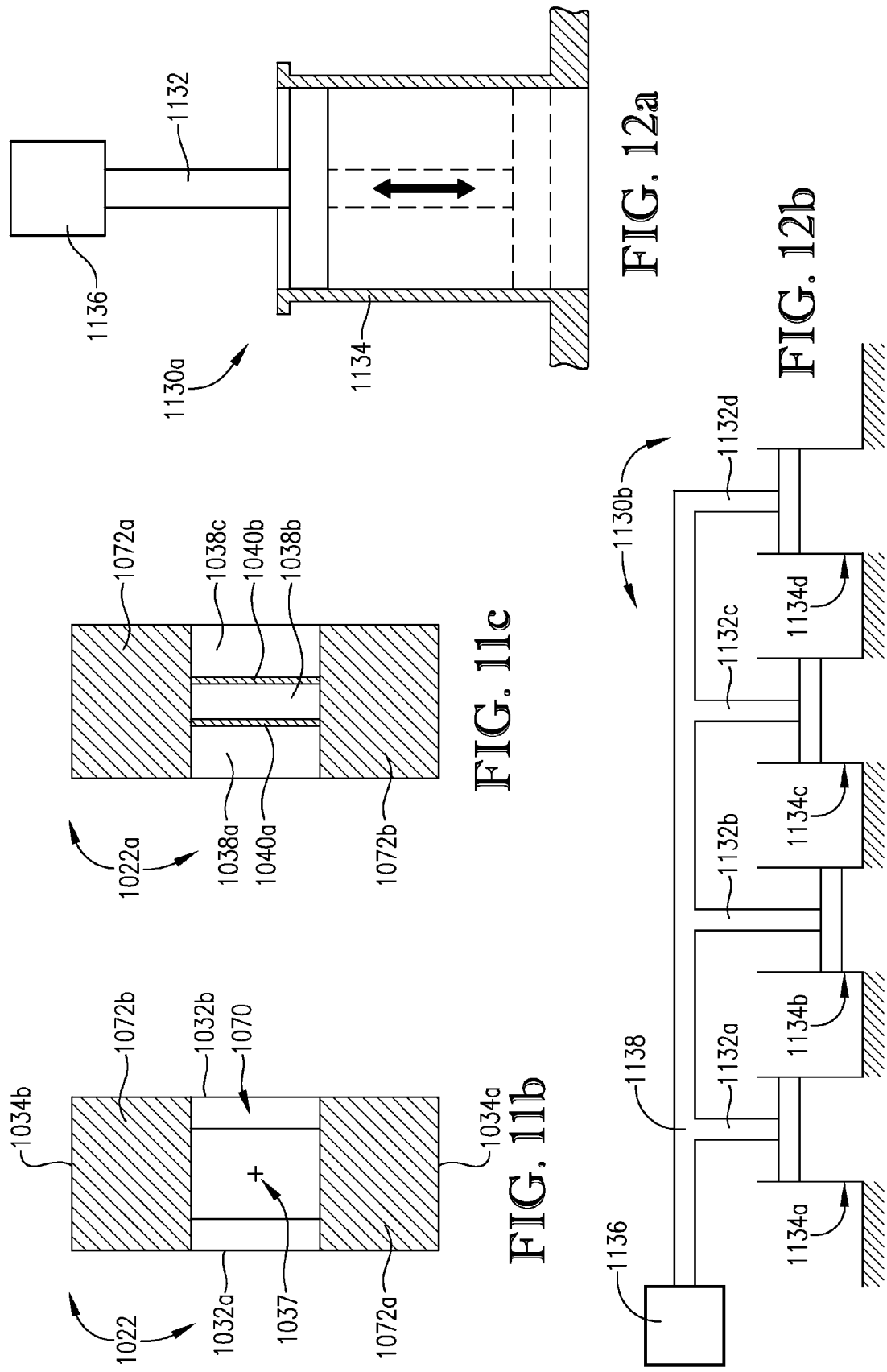

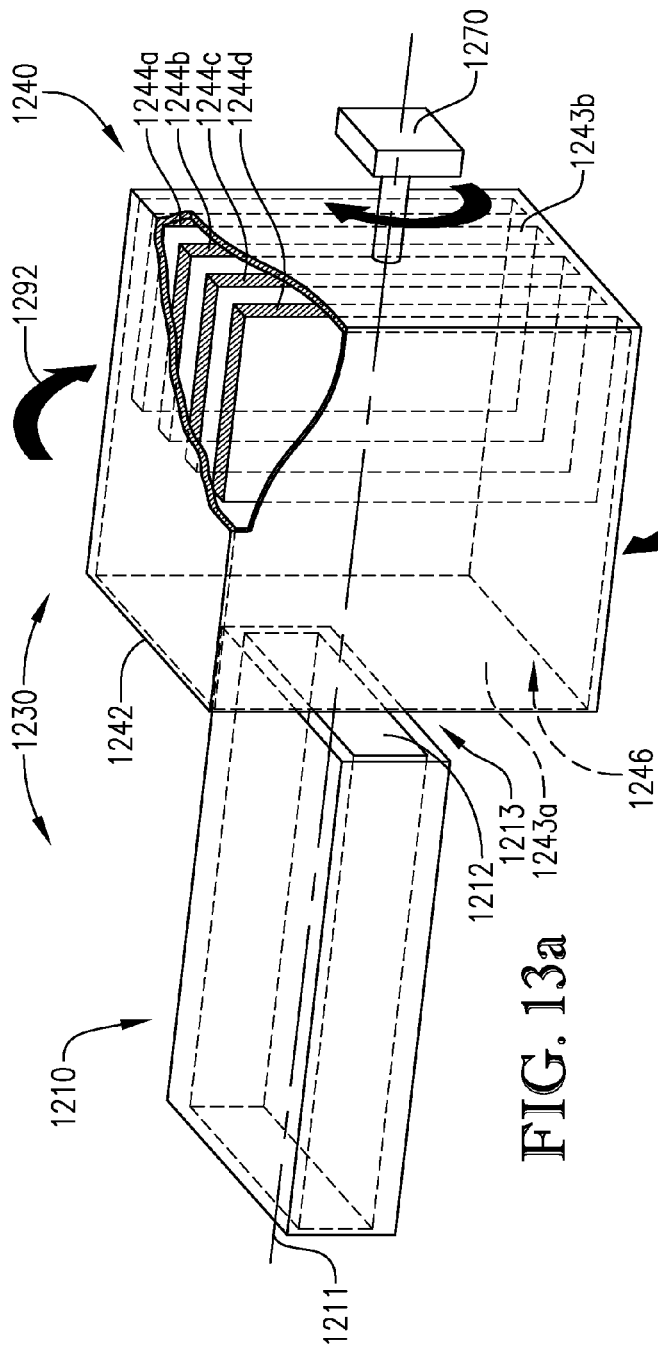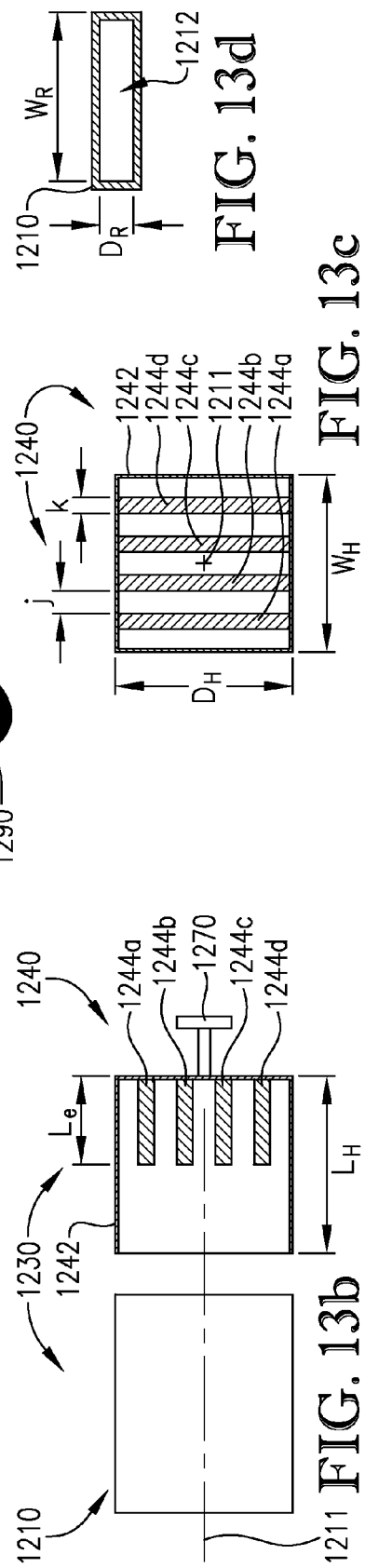

OPTIMIZED MOTION AND LOCATION OF INTENSE MICROWAVE FIELDS WITHIN A HEATING SYSTEM

CROSS-REFERENCE TO RELATED APPLICATIONS

This application claims priority to U.S. Provisional Patent Application Nos. 61/610,708; 61/610,729; 61/610,739; 61/610,745; 61/610,756; 61/610,767; 61/610,776; 61/610,787; 61/610,794; 61/610,804; 61/610,821; 61/610,830, all filed on Mar. 14, 2012, the disclosures of which are incorporated herein by reference.

FIELD OF THE INVENTION

This invention relates to microwave systems for heating one or more objects, articles, and/or loads.

BACKGROUND

Electromagnetic radiation, such as microwave radiation, is a known mechanism for delivering energy to an object. The ability of electromagnetic radiation to penetrate and heat an object in a rapid and effective manner has proven advantageous in many chemical and industrial processes. Because of its ability to quickly and thoroughly heat an article, microwave energy has been employed in heating processes wherein the rapid achievement of a prescribed minimum temperature is desired, such as, for example, pasteurization and/or sterilization processes. Further, because microwave energy is generally non-invasive, microwave heating may be particularly useful for heating 'sensitive' dielectric materials, such as food and pharmaceuticals. However, to date, the complexities and nuances of safely and effectively applying microwave energy, especially on a commercial scale, have severely limited its application in several types of industrial processes.

Thus, a need exists for an efficient, consistent, and cost effective industrial-scale microwave heating system suitable for use in a wide variety of processes and applications.

SUMMARY

One embodiment of the present invention concerns a variable phase short circuit device for use in a microwave heating system. The device comprises a fixed section defining a first substantially rectangular opening and a rotatable section comprising a housing and a plurality of spaced-apart, substantially parallel plates received in the housing. The housing comprises opposite first and second end and the first end defines a second opening adjacent to the first opening of the fixed section. Each of the plates is coupled to the second end of the housing and extends generally toward the first and the second openings. The rotatable section is configured to be rotated relative to the fixed section on an axis of rotation that extends through the first and the second openings.

Another embodiment of the present invention concerns a method for heating a plurality of articles in a microwave heating system comprising the steps of (a) passing the articles through a heating zone of a microwave chamber via a conveyance system, wherein each of the articles is maintained within the heating zone for an article residence time ($\tau$); (b) generating microwave energy with one or more microwave generators; (c) passing at least a portion of the microwave energy through a phase shifting device configured to cyclically shift the phase of the microwave energy at a phase shifting rate (t); (d) discharging at least a portion of the microwave energy exiting the phase shifting device into the heating zone via at least one microwave launcher; and (e) heating the articles in the heating zone with at least a portion of the microwave energy discharged therein, wherein the ratio of the article residence time to the phase shifting rate ($\tau$:t) is at least 4:1.

BRIEF DESCRIPTION OF THE DRAWINGS

FIG. 1a is process flow diagram depicting one embodiment of a microwave heating system for heating one or more articles, particularly illustrating a system comprising a thermalization zone, a microwave heating zone, an optional holding zone, a quench zone, and a pair of pressure adjustment zones;

FIG. 1b is a schematic diagram of a microwave heating system 10 configured according to one embodiment of the present invention, particularly each of the zones of microwave heating system 10 outlined in the diagram provided in FIG. 1a;

FIG. 5a is a partial side cut-away view of a locking gate device configured according to one embodiment of the present invention, particularly showing the gate assembly in an open position;

FIG. 5b is a partial side cut-away view of the locking gate device depicted in FIG. 5a, particularly showing the gate assembly in a closed position with the sealing plates in a retracted position;

FIG. 5c is a partial side cut-away view of the locking gate device depicted in FIGS. 5a and 5b, particularly showing the gate assembly in a closed position with the sealing plates in an extended position;

FIG. 5d is an enlarged partial view of the gate assembly shown in FIGS. 5a-c, particularly illustrating one embodiment of a bearing used to move the sealing plates of the gate assembly;

FIG. 9a is an isometric view of a microwave launcher configured according to one embodiment of the present invention;

FIG. 9b is a longitudinal side view of the microwave launcher depicted in FIG. 9a;

FIG. 10b is a vertical cross-sectional view of the microwave launcher depicted in FIG. 10a, particularly illustrating the multiple microwave outlets;

FIG. 10c is a vertical cross-sectional view of the microwave launcher depicted in FIGS. 10a and 10b, particularly showing the pair of dividing septa used to create individual microwave pathways between the inlet and multiple outlets of the microwave launcher;

FIG. 11a is an isometric view of a microwave launcher configured according to yet another embodiment of the present invention, particularly showing an integrated inductive iris disposed between the inlet and outlet of the launcher;

FIG. 11b is a horizontal cross-sectional view of the microwave launcher depicted in FIG. 11a;

FIG. 11c is a horizontal cross-sectional view of another microwave launcher similar to the launcher depicted in FIG. 11a, but including a pair of dividing septa in addition to an inductive iris disposed between the inlet and outlet of the launcher;

FIG. 12a is a side cut-away view of a phase shifting device configured according to one embodiment of the present invention, particularly illustrating a plunger-type tuning device that includes a single plunger;

FIG. 12b is a schematic side cut-away view of a phase shifting device configured according to another embodiment of the present invention, particularly illustrating a plunger-type tuning device including a plurality of plungers driven by a common rotatable shaft;

FIG. 13a is a side perspective view of a phase shifting device configured according to yet another embodiment of the present invention, particularly illustrating a rotatable phase shifting device;

FIG. 13b is a longitudinal cross-sectional view of the rotatable phase shifting device depicted in FIG. 13a;

FIG. 13c is a lateral cross-sectional view of the rotatable section of the rotatable phase shifting device depicted in FIGS. 13a and 13b, particularly showing the width and spacing of the plates disposed within the housing;

FIG. 13d is an lateral cross-sectional view of the fixed section of the rotatable phase shifting device depicted in FIGS. 13a and 13b, particularly illustrating the dimensions of the fixed section;

DETAILED DESCRIPTION

Figure 2A:
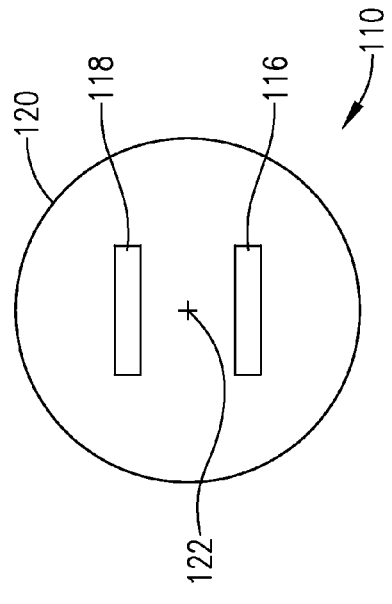
FIG. 2a is a cross-sectional schematic end view of a process vessel configured according to one embodiment of the present invention, particularly illustrating a conveyance system including a pair of convey lines arranged in a side-by-side configuration.

Microwave processes and systems for heating a plurality of articles according to various embodiments of the present invention are described below. Examples of suitable articles to be heated in systems and processes of the present invention can include, but are not limited to, foodstuffs, medical fluids, and medical instruments. In one embodiment, microwave systems described herein can be used for the pasteurization and/or sterilization of the articles being heated. In general, pasteurization involves rapid heating of an article or articles to a minimum temperature between 80° C. and 100° C., while sterilization involves heating one or more articles to a minimum temperature between 100° C. to 140° C. However, in one embodiment, pasteurization and sterilization may take place simultaneously or nearly simultaneously and many processes and systems can be configured to both pasteurize and sterilize one or more articles. Various embodiments of microwave systems and processes configured to heat one or more types of articles will now be discussed in detail, with reference to the Figures.

Turning now to FIGS. 1a and 1b, a schematic representation of the major steps in a microwave heating process according to one embodiment of the present invention is depicted in FIG. 1a, while FIG. 1b depicts one embodiment of a microwave system 10 operable to heat a plurality of articles according to the process outlined in FIG. 1a. As shown in FIGS. 1a and 1b, one or more articles can initially be introduced into a thermalization zone 12, wherein the articles can be thermalized to a substantially uniform temperature. Once thermalized, the articles can then be optionally passed through a pressure adjustment zone 14a before being introduced into a microwave heating zone 16. In microwave heating zone 16, the articles can be rapidly heated using microwave energy discharged into at least a portion of the heating zone by one or more microwave launchers, generally illustrated as launchers 18 in FIG. 1b. The heated articles can then optionally be passed through a holding zone 20, wherein the articles can be maintained at a constant temperature for a specified amount of time. Subsequently, the articles can then be passed to a quench zone 22, wherein the temperature of the articles can be quickly reduced to a suitable handling temperature. Thereafter, the cooled articles can optionally be passed through a second pressure adjustment zone 14b before being removed from system 10 and further utilized.

Microwave system 10 can be configured to heat many different types of articles. In one embodiment, the articles heated in microwave system 10 can comprise foodstuffs, such as, for example, fruits, vegetables, meats, pastas, pre-made meals, and even beverages. In other embodiments, the articles heated in microwave system 10 can comprise packaged medical fluids or medical and/or dental instruments. The articles processed within microwave heating system 10 can be of any suitable size and shape. In one embodiment, each article can have a length (longest dimension) of at least about 2 inches, at least about 4 inches, at least about 6 inches and/or not more than about 18 inches, not more than about 12 inches, or not more than about 10 inches; a width (second longest dimension) of at least about 1 inch, at least about 2 inches, at least about 4 inches and/or not more than about 12 inches, not more than about 10 inches, or not more than about 8 inches; and/or a depth (shortest dimension) of at least about 0.5 inches, at least about 1 inch, at least about 2 inches and/or not more than about 8 inches, not more than about 6 inches, or not more than about 4 inches. The articles can comprise individual items or packages having a generally rectangular or prism-like shape or can comprise a continuous web of connected items or packages passed through microwave system 10. The items or packages may be constructed of any material, including plastics, cellulosics, and other microwave-transparent materials, and can be passed through microwave system 10 via one or more conveyance systems, embodiments of which will be discussed in detail below.

According to one embodiment of the present invention, each of the above-described thermalization, microwave heating, holding, and/or quench zones 12, 16, 20, and 22 can be defined within a single vessel, as generally depicted in FIG. 1b, while, in another embodiment, at least one of the above-described stages can be defined within one or more separate vessels. According to one embodiment, at least one of the above-described steps can be carried out in a vessel that is at least partially filled with a fluid medium in which the articles being processed can be at least partially submerged. The fluid medium can be a gas or a liquid having a dielectric constant greater than the dielectric constant of air and, in one embodiment, can be a liquid medium having a dielectric constant similar to the dielectric constant of the articles being processed. Water (or liquid media comprising water) may be particularly suitable for systems used to heat edible and/or medical devices or articles. In one embodiment, additives, such as, for example, oils, alcohols, glycols, and salts may optionally be added to the liquid medium to alter or enhance its physical properties (e.g., boiling point) during processing, if needed.

Microwave system 10 can include at least one conveyance system (not shown in FIGS. 1a and 1b) for transporting the articles through one or more of the processing zones described above. Examples of suitable conveyance systems can include, but are not limited to, plastic or rubber belt conveyors, chain conveyors, roller conveyors, flexible or multiflexing conveyors, wire mesh conveyors, bucket conveyors, pneumatic conveyors, screw conveyors, trough or vibrating conveyors, and combinations thereof. The conveyance system can include any number of individual convey lines and can be arranged in any suitable manner within the process vessels. The conveyance system utilized by microwave system 10 can be configured in a generally fixed position within the vessel or at least a portion of the system can be adjustable in a lateral or vertical direction.

Turning now to FIGS. 2a-2d, embodiments of a process vessel 120 that includes a conveyance system 110 disposed therein are provided. In one embodiment generally depicted in FIGS. 2a and 2b, conveyance system 110 includes a pair of laterally spaced, substantially parallel convey lines 112, 114 positioned in a generally side-by-side configuration within vessel 120. As shown in the top, cut-away view of vessel 120 in FIG. 2b, convey lines 112 and 114 may be laterally spaced from each other and may be positioned on both sides of a convey axis 122, which extends along the length of vessel 120 in the direction of conveyance of the articles passing therethrough. Although shown in FIG. 2a as being at generally the same vertical elevation within vessel 120, it should be understood that, in one embodiment, convey lines 112, 114 may also be positioned at different vertical elevations. Additionally, conveyance system 110 depicted in FIGS. 2a and 2b may also include multiple pairs of laterally spaced convey lines (embodiment not shown), such that the pairs of laterally spaced convey lines are vertically spaced from each other along the vertical dimension of vessel 120.

Figure 2C:
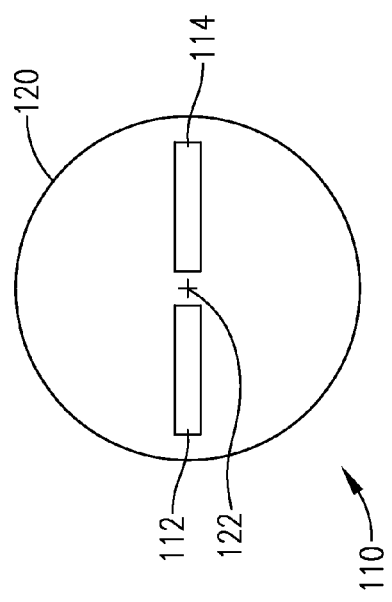
FIG. 2c is a cross-sectional schematic end view of another process vessel configured according to another embodiment of the present invention, particularly illustrating a conveyance system including a pair of convey lines arranged in a stacked configuration.
Figure 2B:
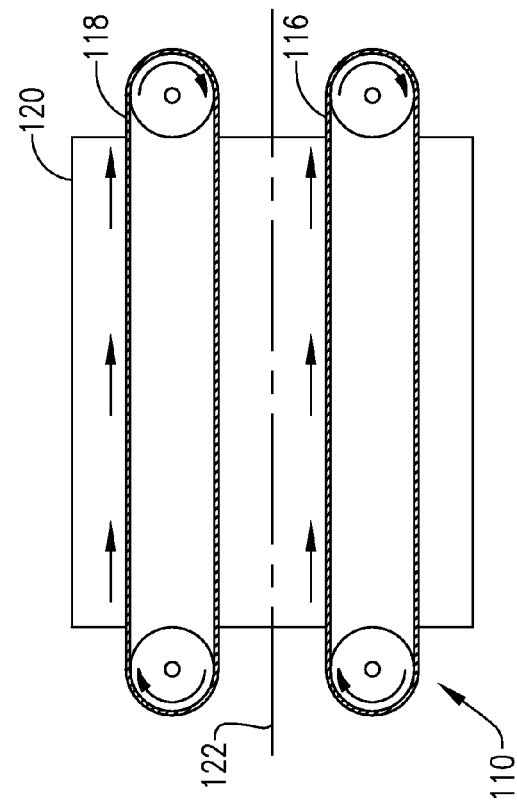
FIG. 2b is a schematic top cut-away view of the process vessel shown in FIG. 2a, particularly illustrating the laterally-spaced arrangement of the convey lines relative to the convey axis extending through the vessel.
Figure 2D:
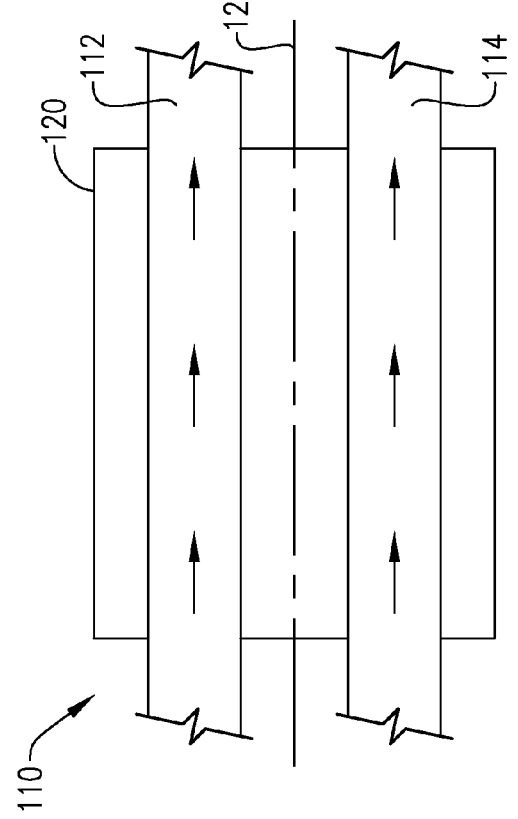
FIG. 2d is a schematic side cut-away view of the process vessel shown in FIG. 2c, particularly illustrating the vertically-spaced arrangement of the convey lines relative to convey axis extending through the vessel.

Another embodiment of a conveyance system 110 that includes a pair of vertically-spaced, substantially parallel convey lines 116, 118 positioned in a stacked arrangement within the interior of vessel 120, is shown in FIGS. 2c and 2d. Convey lines 116 and 118 may be configured above and below convey axis 122, which may generally extend along the length of vessel 120, as shown in the cutaway side view of vessel 120 provided in FIG. 2d. Additionally, in a similar manner as previously described, vessel 120 shown in FIGS. 2c and 2d may also include multiple pairs of convey lines, laterally spaced from one another within the vessel. Further, each convey line of the pair may or may not be offset from the other in a lateral direction. In a further embodiment (not shown), vessel 120 may include a single convey line, positioned in the middle one-third of the internal volume of vessel 120, or positioned at or near the centerline of the vessel. Additional details of conveyance systems according to several embodiments of the present invention will be discussed in detail below.

Figure 3:
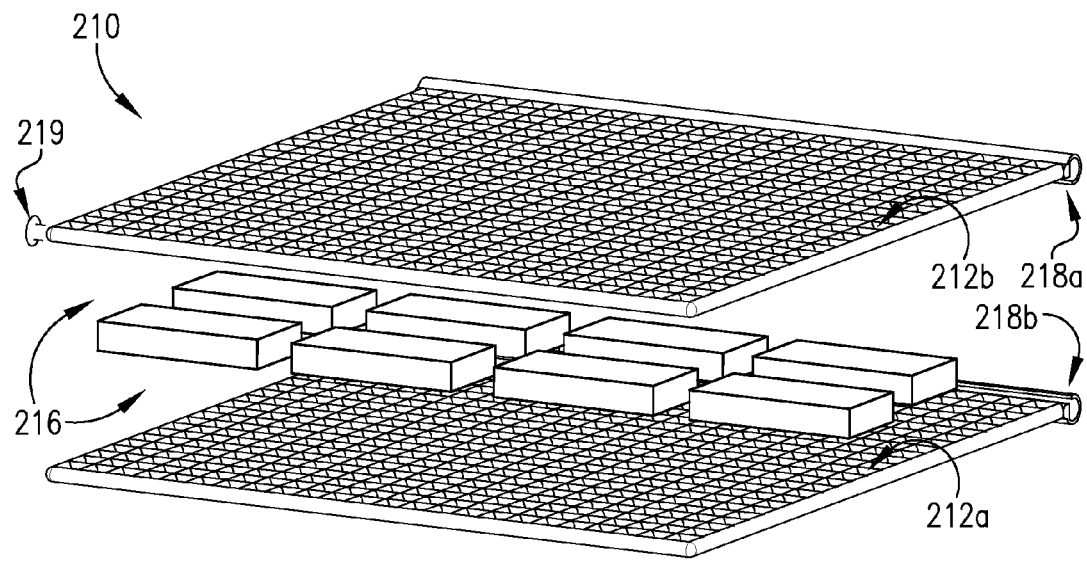
FIG. 3 is a perspective view of a carrier according to one embodiment of the present invention configured to secure and transport the articles being heated through a liquid-filled process vessel.

When a conveyance system is used to transport articles through a liquid-filled process vessel, one or more carriers or other securing mechanisms can be used to control the position of the articles during passage through the liquid medium. One embodiment of a suitable carrier 210 is illustrated in FIG. 3. As shown in FIG. 3, carrier 210 comprises a lower securing surface 212a and an upper securing surface 212b configured to secure any suitable number of articles 216 therebetween. In one embodiment, upper and/or lower surfaces 212b,a can have a meshed, grid, or grated structure, as generally depicted in FIG. 3, while, in another embodiment, one or both surfaces 212a,b can be a substantially continuous surface. Carrier 210 can be constructed of plastic, fiberglass, or any other dielectric material and, in one embodiment, may be made of one or more microwave-compatible and/or microwave-transparent materials. In some embodiments, the material may be a lossy material. In some embodiments, carrier 210 can comprise substantially no metal.

Lower and upper securing surfaces 212a, 212b may be attached to one another by a securing device, shown as a fastener 219 in FIG. 3, and, as assembled, carrier 210 may be attached or secured to the conveyance system (not shown in FIG. 3) according to any suitable attachment mechanism. In one embodiment, at least one side (or edge) of carrier 210 can include one or more attachment mechanisms, such as, for example, upper and lower hooks 218a, 218b shown in FIG. 3, for securing carrier 210 to a portion (e.g., a bar, a rail, a belt, or a chain) of the conveyance system (not shown). Depending on the thickness and/or weight of articles 216, carrier 210 may only include one of hooks 218a, 218b for securing carrier 210 onto the conveyance system. The conveyance system used to transport articles 216 may be configured to transport multiple carriers along one or more conveyance lines and the carriers may be arranged in a side-by-side, laterally-spaced configuration and/or in a vertically-spaced, stacked configuration as described previously. When the conveyance system includes a plurality of convey lines, each convey line may include a single carrier for holding a plurality of articles 216, or each convey line may hold multiple carriers stacked or laterally spaced from each other.

Referring back to FIGS. 1a and 1b, the articles introduced into microwave system 10 are initially introduced into thermalization zone 12, wherein the articles are thermalized to achieve a substantially uniform temperature. In one embodiment, at least about 85 percent, at least about 90 percent, at least about 95 percent, at least about 97 percent, or at least about 99 percent of all the articles withdrawn from thermalization zone 12 have a temperature within about 5° C., within about 2° C., or within 1° C. of one another. As used herein, the terms "thermalize" and "thermalization" generally refer to a step of temperature equilibration or equalization. Depending on the initial and desired temperature of the articles being thermalized, the temperature control system of thermalization zone 12, illustrated in FIG. 1a as heat exchanger 13, can be a heating and/or cooling system. In one embodiment, the thermalization step can be carried out under ambient temperature and/or pressure, while, in another embodiment, thermalization can be carried out in a pressurized and/or liquid-filled thermalization vessel at a pressure of not more than about 10 psig, not more than about 5 psig, or not more than about 2 psig. Articles undergoing thermalization can have an average residence time in thermalization zone 12 of at least about 30 seconds, at least about 1 minute, at least about 2 minutes, at least about 4 minutes and/or not more than about 20 minutes, not more than about 15 minutes, or not more than about 10 minutes. In one embodiment, the articles withdrawn from thermalization zone 12 can have a temperature of at least about 20° C., at least about 25° C., at least about 30° C., at least about 35° C. and/or not more than about 70° C., not more than about 65° C., not more than about 60° C., or not more than about 55° C.

In one embodiment wherein thermalization zone 12 and microwave heating zone 16 are operated at substantially different pressures, the articles removed from thermalization zone 12 can first be passed through a pressure adjustment zone 14a before entering microwave heating zone 16, as generally depicted in FIGS. 1a and 1b. Pressure adjustment zone 14a can be any zone or system configured to transition the articles being heated between an area of lower pressure and an area of higher pressure. In one embodiment, pressure adjustment zone 14a can be configured to transition the articles between two zones having a pressure difference of at least about 1 psi, at least about 5 psi, at least about 10 psi and/or not more than about 50 psi, not more than about 45 psi, not more than about 40 psi, or not more than about 35 psi. In one embodiment, microwave system 10 can include at least two pressure adjustment zones 14a,b to transition the articles from an atmospheric pressure thermalization zone to a heating zone operated at an elevated pressure before returning the articles back to atmospheric pressure, as described in detail below.

Figure 4A:
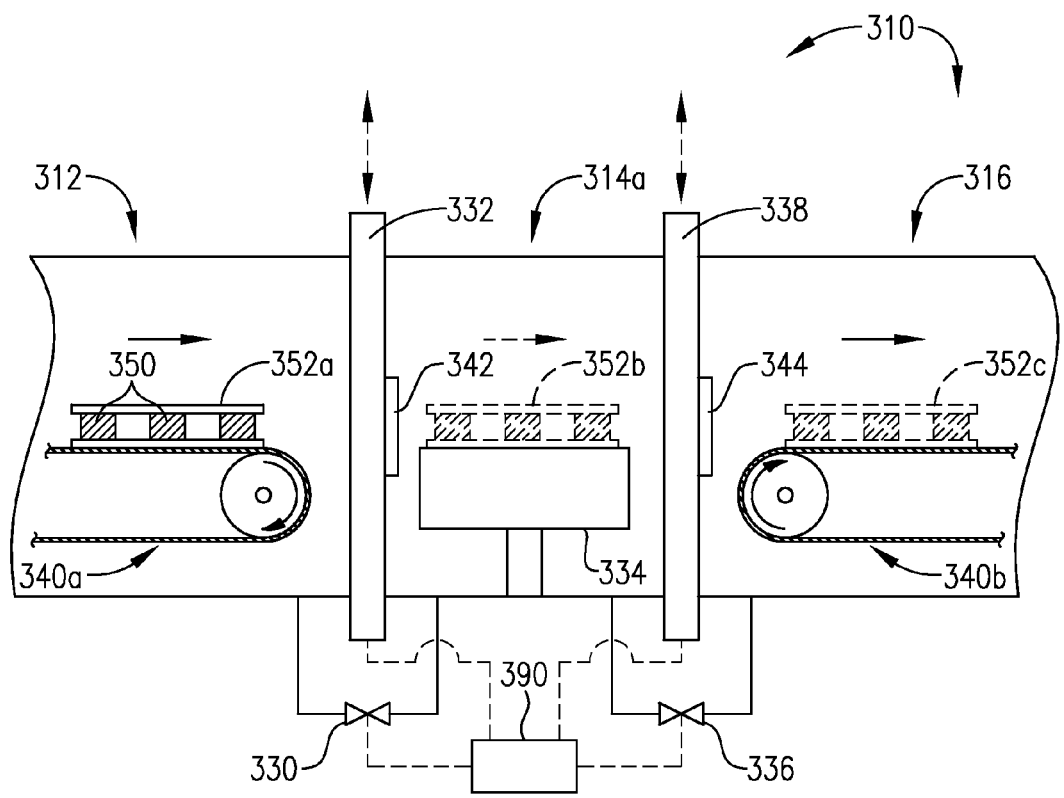
FIG. 4a is a partial side cut-away view of one embodiment of a microwave heating system that includes a pressure adjustment zone configured to transport one or more articles from the thermalization zone to the microwave heating zone of the heating system using a carrier transfer system.

One embodiment of a pressure adjustment zone 314a disposed between a thermalization zone 312 and a microwave heating zone 316 of a microwave heating system 310 is illustrated in FIG. 4a. Pressure adjustment zone 314a is configured to transition a plurality of articles 350, which may be secured within at least one carrier, from lower-pressure thermalization zone 312 to higher-pressure microwave heating zone 316. Although shown in FIG. 4a as being a single carrier 352a, it should be understood that pressure adjustment zone 314a may be configured to receive more than one carriers. In one embodiment, the carriers may be received simultaneously, such that pressure adjustment zone 314a contains multiple carriers at one time. In another embodiment, multiple carriers may be lined up and ready, for example within thermalization zone 312, for being transitioned through pressure adjustment zone 314a, details of which will now be discussed below.

In operation, one or more carriers 352a can be transitioned from thermalization zone 312 to microwave heating zone 316 by first opening an equilibration valve 330 and allowing the pressure between thermalization zone 312 and pressure adjustment zone 314a to equalize. Next, a gate device 332 can be opened to allow carrier 352a to be moved from a convey line 340a disposed within thermalization zone 312 onto a platform 334 within pressure adjustment zone 314a, as generally shown by the dashed-line carrier 352b in FIG. 4a.

Thereafter, gate device 332 and equilibrium valve 330 can be closed in sequence, re-isolating pressure adjustment zone 314a from thermalization zone 312. Subsequently, another equilibration valve 336 can be opened to allow the pressure between pressure adjustment zone 314a and microwave heating zone 316 to equalize. Once equilibrium is achieved, another gate device 338 can be opened to permit carrier 352b to be moved onto another conveyance system 340b disposed within microwave heating zone 316, as generally shown by dashed-line carrier 352c in FIG. 4a. Subsequently, gate device 338 and equalization valve 336 may be closed in sequence, re-isolating microwave heating zone 316 from pressure adjustment zone 314a. The process may then be repeated to transport additional carriers from thermalization zone 312 to microwave heating zone 316 as needed.

According to one embodiment, each of microwave heating zone 316 and thermalization zone 312 can be filled with a non-compressible fluid or liquid, such as, for example, water or solutions including water. As used herein, the term "filled" denotes a configuration where at least 50 percent of the specified volume is filled with the filling medium. The "filling medium" can be a liquid, typically an incompressible liquid, and may be or include, for example, water. In certain embodiments, "filled" volumes can be at least about 75 percent, at least about 90 percent, at least about 95 percent, or 100 percent full of the filling medium. When thermalization zone 312 and/or microwave heating zone 316 are filled with an incompressible fluid, gate devices 332, 338 and/or pressure adjustment zone 314a may also include two or more one-way flaps or valves, shown as valves or flaps 342, 344 in FIG. 4a, for preventing substantial fluid leakage between thermalization zone 312 and microwave heating zone 316 when gate devices 332 and 338 are open and carrier 352 is passed therethrough.

Figure 4B:
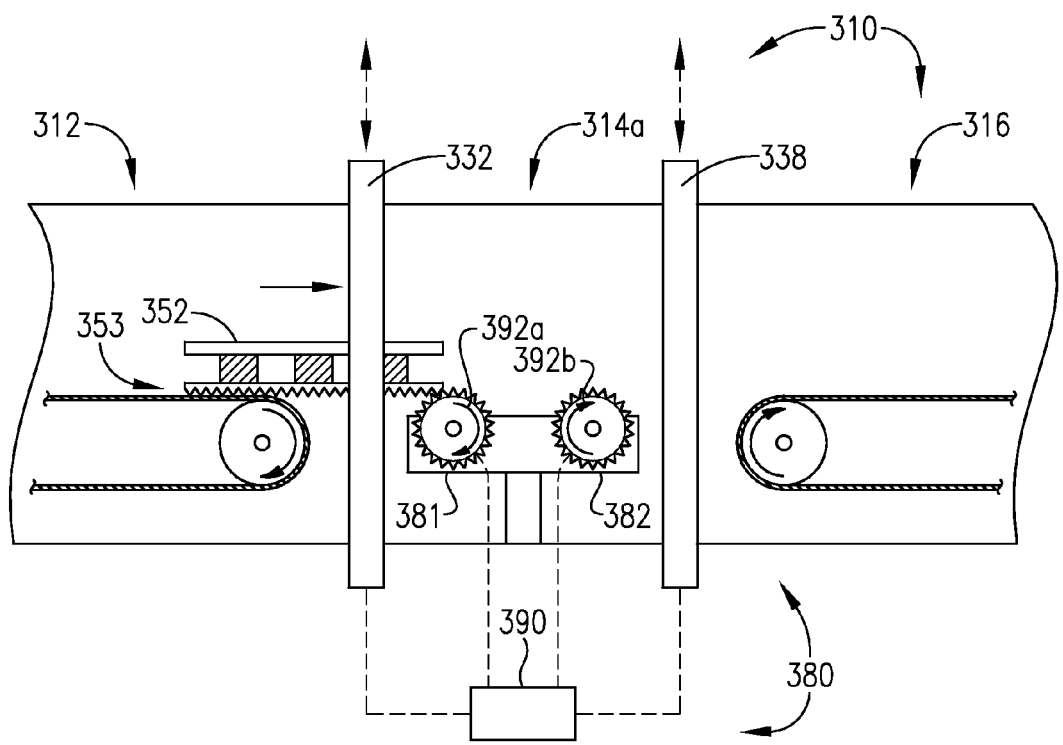
FIG. 4b is a partial side cut-away view of another embodiment of a microwave heating system including a pressure adjustment zone similar to the one depicted in FIG. 4a, but particularly illustrating a carrier transfer system disposed nearly entirely within the pressure adjustment zone.
Figure 4C:
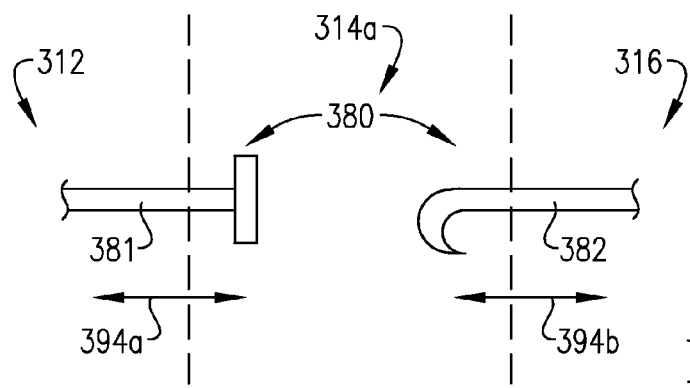
FIG. 4c is a partial schematic view of the pressure adjustment zone similar to the ones depicted in FIGS. 4a and 4b, but illustrating another embodiment of the carrier transfer system for moving the articles from the thermalization zone to the microwave heating zone.
Figure 4D:
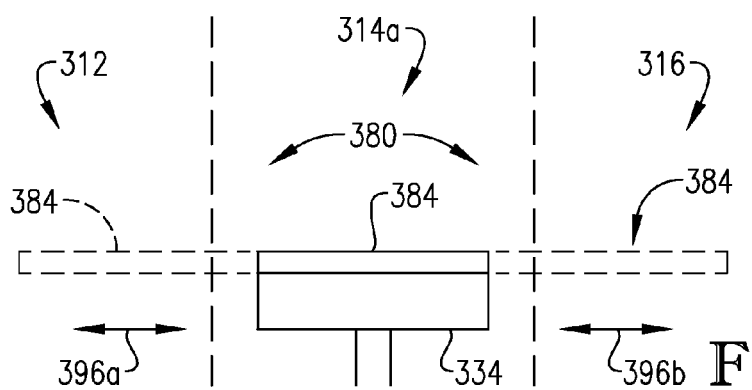
FIG. 4d is a partial schematic view of the pressure adjustment zone similar to the ones depicted in FIGS. 4a and 4b, but illustrating yet another embodiment of the carrier transfer system for moving the articles from the thermalization zone to the microwave heating zone.

The transportation of carrier 352 from thermalization zone 312 through pressure adjustment zone 314a and into microwave heating zone 316 can be accomplished via one or more automatic article transfer systems, several embodiments of which are illustrated in FIGS. 4b-4d. In some embodiments, automatic transfer system 380 can include one or more transfer devices, disposed within thermalization zone 312, pressure adjustment zone 314a, and/or microwave heating zone 316 for moving carrier 352 into and/or out of pressure adjustment zone 314a. In one embodiment shown in FIG. 4b, transfer system 380 includes two gear transfer devices 381, 382 configured to engage teeth 353 disposed along the lower edge of carrier 352 and rotate, as indicated by the arrows 392a,b, to pull carrier 352 into out of thermalization zone 312 and/or push carrier 352 into microwave heating zone 316. As shown in FIG. 4b, first and second gear transfer devices 381, 382 remain substantially stationary (in terms of lateral motion) during the transportation of carrier 352 and are nearly entirely, or entirely, disposed within pressure adjustment zone 314a.

In contrast, some embodiments of automatic transfer system 380 can include one or more transfer devices that are laterally shiftable (i.e., movable in the direction of transport) during transport of carrier 352 into and/or out of pressurize adjustment zone 314a. As depicted in one embodiment shown in FIG. 4c, a portion of the automatic transfer system 380 may be disposed in thermalization zone 312 and/or microwave heating zone 316 and can be configured for extension into and retraction out of pressure adjustment zone 314a. In the system 380 shown in FIG. 4c, the transfer devices include a pusher arm 381 configured to push carrier 352 into pressure adjustment zone 314a and a puller arm 382 for pulling carrier 352 into microwave heating zone 316. Neither pusher arm 381 nor puller arm 382 are disposed within pressure adjustment zone 314a, but instead, each is configured to extend into and retract out of pressure adjustment zone 314a, as generally shown by arrows 394a,b in FIG. 4c.

According to another embodiment depicted in FIG. 4d, automatic transport system 380 includes a platform 334 having a movable portion 384, which is configured to be extended into and retracted out of thermalization 312 and/or microwave heating zone 316 to thereby transport carrier 352 into and out of thermalization and microwave heating zones 312, 316, as generally shown by arrows 396a and 396b. In contrast to the embodiment shown in FIG. 4c, automatic transfer system 380 depicted in FIG. 4d is primarily disposed within pressure adjustment zone 314a and is configured to extend out of and retract back into pressure adjustment zone 314a.

Regardless of the specific configuration of the transfer devices utilized by automatic article transfer system 380, the transfer system can be automated, or controlled, by an automatic control system 390, as illustrated in FIGS. 4a and 4b. Although not specifically depicted in the embodiments illustrated in FIGS. 4c and 4d, it should be understood that such control systems 390 may also be employed in these embodiments. Automatic control system 390 can be used to control the motion and/or timing of at least one of first and second equilibration valves 330, 336, first and second gate valves 332, 338, and first and second transfer devices 381, 382 of the automatic article transfer system 380. In one embodiment, control system 390 can adjust the position, speed, and/or timing of these devices or elements in order to ensure that the carriers within the system move in an uninterrupted and consistent manner.

Turning now to FIGS. 5a-5d, one embodiment of a locking gate device 420, suitable for use as gate device 332 and/or 338 in the portion of microwave system 310 depicted in FIGS. 4a and 4b, is provided. Locking gate valve device 420 is illustrated in FIGS. 5a-d as generally comprising a pair of spaced apart fixed members 410, 412 that present opposing sealing surfaces 414a,b and that define a gate-receiving space 416 therebetween. The spaced apart fixed members 410, 412 can each define a flow-through opening 418a,b, which are circumscribed by one of sealing surfaces 414a,b. Each of flow-through openings 418a,b are substantially aligned with one another such that the articles can pass through the cumulative opening when gate valve device 420 is open.

Locking gate device 420 further comprises a gate assembly 422, which is configured to be received within gate-receiving space 416 and is shiftable therein between a closed position (as shown in FIGS. 5b and 5c), wherein gate assembly 422 substantially blocks flow-through openings 418a,b, and an open position (as shown in FIG. 5a), wherein gate assembly 422 does not substantially block flow-through openings 418a, b. In one embodiment, gate assembly 422 comprises a pair of spaced apart sealing plates 424, 426 and a drive member 428 disposed between sealing plates 424, 426. When gate assembly 422 is configured in the closed position, drive member 428 is shiftable, relative to sealing plates 424, 426, between a retracted position (as shown in FIG. 5*b*) and an extended position (as shown in FIG. 5*c*). In one embodiment shown in FIGS. 5*a*-*c*, gate assembly 422 comprises at least one pair of bearings 430 disposed within the space defined between opposing sealing plates 424, 426, which is positioned in gate receiving space 416 when gate assembly 422 is in a closed position, as particularly shown in FIGS. 5*b* and 5*c*. When drive member 428 is shifted between a retracted position as illustrated in FIG. 5*b* to an extended position as depicted in FIG. 5*c*, at least one bearing of pair 430 can force at least one of sealing plates 424, 426 outwardly, away from one another and into a sealed position, as shown in FIG. 5*c*.

In one embodiment, one or more of the bearings of pair 430 can be secured, attached, or at least partially housed within at least one of sealing plates 424, 426 and/or drive member 428. According to one embodiment, at least one of the bearings 430 *a* can be fixedly attached to drive member 428, as depicted in the enlarged partial view of gate assembly 422 provided in FIG. 5*d*. As drive member 428 shifts downwardly into gate receiving space 416, one of the bearings 430*a* from the pair can contact one of sealing plates 424, 426 (shown as plate 426 in FIG. 5*d*) and can move along a ramp (or slot) 427 therein. As the bearing travels through the slot 427 (or along the ramp 427), outward pressure is exerted on sealing plate 426, thereby moving it in a direction as indicated by arrow 460. Although shown as including only a single pair of bearings 430, it should be understood that any number of bearings, positioned along the vertical length of drive member 428 and/or sealing members 424, 426 can be used.

When in a sealed position, as shown in FIG. 5*c*, at least a portion of sealing plates 424, 426 engage or physically contact respective opposing sealing surface 414*a,b*, to thereby form a substantially fluid tight seal. In one embodiment, each of sealing plates 424, 426 comprises a resilient seal 423, 425 for engaging sealing surfaces 414*a,b* when sealing plates 424, 426 are in the sealed position. When drive member 428 is shifted from the extended position, as shown in FIG. 5*c*, back to the retracted position, as shown in FIG. 5*b*, sealing plates 424, 426 retract towards one another into the unsealed position, as shown in FIG. 5*b*. In the unsealed position, sealing plates 424, 426 are disengaged from opposing sealing surfaces 414*a,b*, but may remain disposed within gate receiving space 416. In one embodiment, sealing plates 424, 426 can be biased towards the unsealed position and can include at least one biasing device 429 (e.g., a spring or springs) for biasing sealing plates 424, 426 toward the unsealed position.

Referring again to FIGS. 1*a* and 1*b*, the articles exiting thermalization zone 12, and optionally passed through pressure adjustment zone 14*a*, as described above, can then be introduced into microwave heating zone 16. In microwave heating zone 16, the articles can be rapidly heated with a heating source that uses microwave energy. As used herein, the term "microwave energy" refers to electromagnetic energy having a frequency between 300 MHz and 30 GHz. In one embodiment, various configurations of microwave heating zone 16 can utilize microwave energy having a frequency of about 915 MHz or a frequency of about 2.45 GHz, both of which have been generally designated as industrial microwave frequencies. In addition to microwave energy, microwave heating zone 16 may optionally utilize one or more other heat sources such as, for example, conductive or convective heating or other conventional heating methods or devices. However, at least about 85 percent, at least about 90 percent, at least about 95 percent, or substantially all of the energy used to heat the articles within microwave heating zone 16 can be microwave energy from a microwave source.

According to one embodiment, microwave heating zone 16 can be configured to increase the temperature of the articles above a minimum threshold temperature. In one embodiment wherein microwave system 10 is configured to sterilize a plurality of articles, the minimum threshold temperature (and operating temperature of microwave heating zone 16) can be at least about 120° C., at least about 121° C., at least about 122° C. and/or not more than about 130° C., not more than about 128° C., or not more than about 126° C. Microwave heating zone 16 can be operated at approximately ambient pressure, or it can include one or more pressurized microwave chambers operated at a pressure of at least about 5 psig, at least about 10 psig, at least about 15 psig and/or not more than about 80 psig, not more than about 60 psig, or not more than about 40 psig. In one embodiment, the pressurized microwave chamber can be a liquid-filled chamber having an operating pressure such that the articles being heated can reach a temperature above the normal boiling point of the liquid medium employed therein.

The articles passing through microwave heating zone 16 can be heated to the desired temperature in a relatively short period of time, which, in some cases, may minimize damage or degradation of the articles. In one embodiment, the articles passed through microwave heating zone 16 can have an average residence time of at least about 5 seconds, at least about 20 seconds, at least about 60 seconds and/or not more than about 10 minutes, not more than about 8 minutes, or not more than about 5 minutes. In the same or other embodiments, microwave heating zone 16 can be configured to increase the average temperature of the articles being heated by at least about 20° C., at least about 30° C., at least about 40° C., at least about 50° C., at least about 75° C. and/or not more than about 150° C., not more than about 125° C., or not more than about 100° C., at a heating rate of at least about 15° C. per minute (° C./min), at least about 25° C./min, at least about 35° C./min and/or not more than about 75° C./min, not more than about 50° C./min, or not more than about 40° C./min.

Figure 6A:
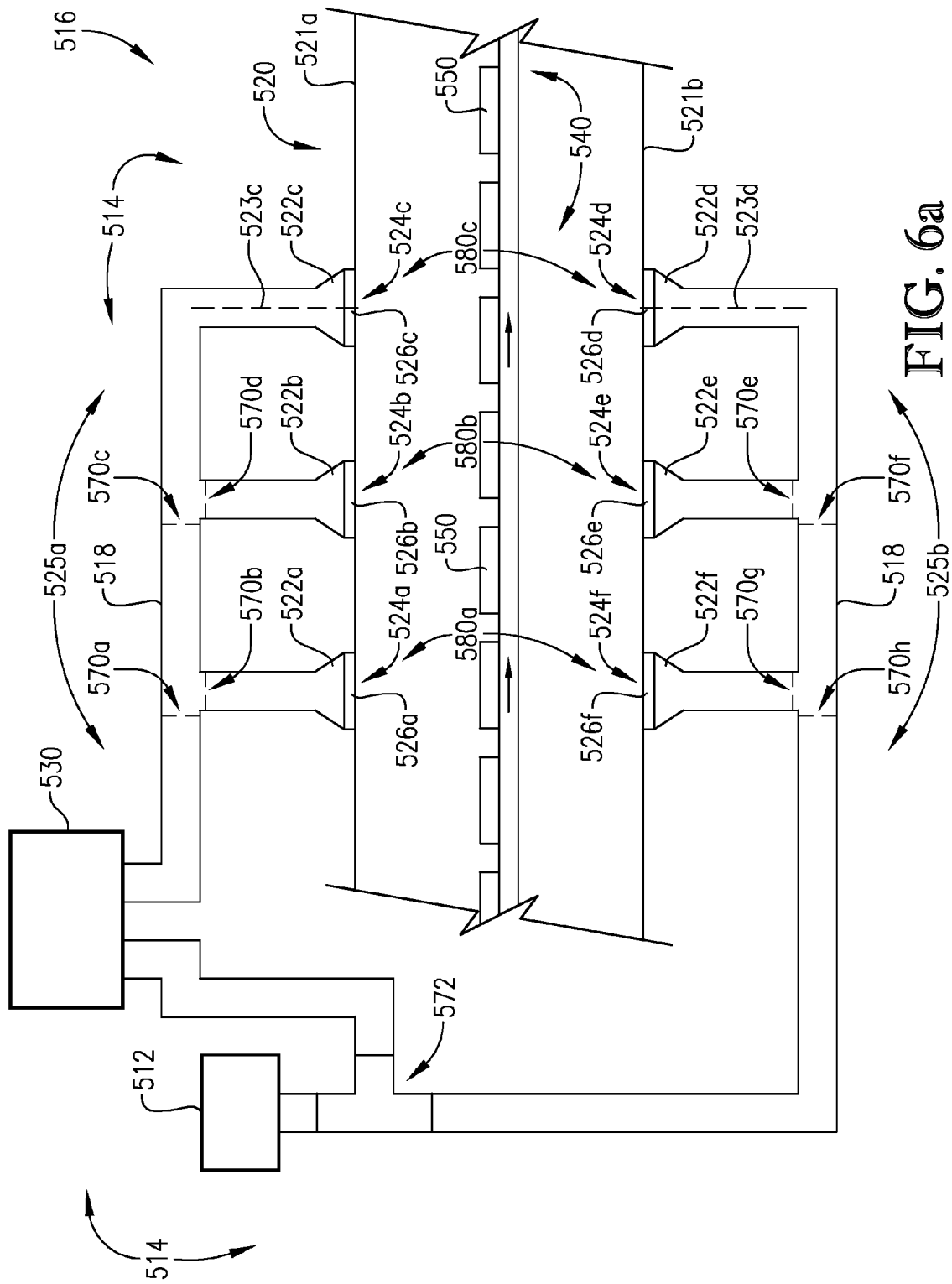
FIG. 6a is a schematic partial side cut-away view of a microwave heating zone configured according to one embodiment of the present invention, particularly illustrating the heating vessel and the microwave distribution system.

Turning now to FIG. 6*a*, one embodiment of a microwave heating zone 516 is illustrated as generally comprising a microwave heating chamber 520, at least one microwave generator 512 for generating microwave energy and a microwave distribution system 514 for directing at least a portion of the microwave energy from generator 512 to microwave chamber 520. Microwave distribution system 514 comprises a plurality of waveguide segments 518 and one or more microwave launchers, shown as launchers 522*a*-*f* in FIG. 6*a*, for discharging microwave energy into the interior of microwave chamber 520. As shown in FIG. 6*a*, microwave heating zone 516 can further comprise a conveyance system 540 for transporting articles 550 to be heated through microwave chamber 520. Each of the components of microwave heating zone 516, according to various embodiments of the present invention, are now discussed in detail immediately below.

Microwave generator 512 can be any suitable device for generating microwave energy of a desired wavelength (λ). Examples of suitable types of microwave generators can include, but are not limited to, magnetrons, klystrons, traveling wave tubes, and gyrotrons. Although illustrated in FIG. 6*a* as including a single generator 512, it should be understood that microwave heating system 516 can include any number of generators arranged in any suitable configuration. For example, in one embodiment, microwave heating zone 516 can include at least 1, at least 2, at least 3 and/or not more than 5, not more than 4, or not more than 3 microwave generators, depending on the size and arrangement of microwave distribution system 514. Specific embodiments of a microwave heating zone including multiple generators will be discussed in detail below.

Microwave chamber 520 can be any chamber or vessel configured to receive a plurality of articles. Microwave chamber 520 can be of any size and may have one of a variety of different cross-sectional shapes. For example, in one embodiment, chamber 520 can have a generally circular or elliptical cross-section, while, in other embodiments, can have a generally square, rectangular, or polygonal cross-sectional shape. In one embodiment, microwave chamber 520 can be a pressurized chamber and, in the same or other embodiments, can be configured to be at least partially filled with a liquid medium (a liquid-filled chamber). Microwave chamber 520 can also be configured to receive at least a portion of the microwave energy discharged from one or more microwave launchers 522 and, in one embodiment, can be configured to permit the creation of a stable (or standing) wave pattern therein. In one embodiment, at least one dimension of microwave chamber 520 can be at least about 0.30λ, at least about 0.40λ, or at least about 0.50λ, wherein λ is the wavelength of the microwave energy discharged therein.

Microwave distribution system 514 comprises a plurality of waveguides or waveguide segments 518 for directing at least a portion of the microwave energy from generator 512 to microwave chamber 520. Waveguides 518 can be designed and constructed to propagate microwave energy in a specific predominant mode, which may be the same as or different than the mode of the microwave energy generated by generator 512. As used herein, the term "mode" refers to a generally fixed cross-sectional field pattern of microwave energy. In one embodiment of the present invention, waveguides 518 can be configured to propagate microwave energy in a $TE_{xy}$ mode, wherein x and y are integers in the range of from 0 to 5. In another embodiment of the present invention, waveguides 518 can be configured to propagate microwave energy in a $TM_{ab}$ mode, wherein a and b are integers in the range of from 0 to 5. It should be understood that, as used herein, the above-defined ranges of a, b, x, and y values as used to describe a mode of microwave propagation are applicable throughout this description. In one embodiment, the predominant mode of microwave energy propagated through waveguides 518 and/or discharged via launchers 522a-f can be selected from the group consisting of $TE_{10}$, $TM_{01}$, and $TE_{11}$.

As shown in FIG. 6a, microwave distribution system 514 further comprises one or more microwave launchers 522a-f, each defining at least one launch opening 524a-f for discharging microwave energy into microwave chamber 520. Although illustrated in FIG. 6a as comprising six microwave launchers 522a-f, it should be understood that microwave distribution system 514 can include any suitable number of launchers arranged in any desirable configuration. For example, microwave distribution system 514 can include at least 1, at least 2, at least 3, at least 4 and/or not more than 50, not more than 30, or not more than 20 microwave launchers. Launchers 522a-f can be the same or different types of launchers and, in one embodiment, at least one of launchers 522a-f can be replaced with a reflective surface (not shown) for reflecting at least a portion of the microwave energy discharged from the other launchers 522 into microwave heating chamber 520.

When microwave distribution system 514 includes two or more launchers, at least some of the launchers may be disposed on generally the same side of microwave chamber 520. As used herein, the term "same-side launchers" refers to two or more launchers positioned on generally the same side of a microwave chamber. Two or more of the same-side launchers may also be axially spaced from one another. As used herein, the term "axially spaced" denotes spacing in the direction of conveyance of the articles through the microwave system (i.e., spacing in the direction of extension of the convey axis). Additionally, one or more launchers 522 may also be laterally spaced from one or more other launchers 522 of the system. As used herein, the term "laterally spaced" shall denote spacing in the direction perpendicular to the direction of conveyance of the articles through the microwave system (i.e., spacing perpendicular to the direction of extension of the convey axis). For example, in FIG. 6a, launchers 522a-c and 522d-f are disposed on respective first and second sides 521a,b of microwave chamber 520 and launcher 522a is axially spaced from launcher 522b and 522c, just as launcher 522e is axially spaced from launchers 522f and 522d.

Additionally, as shown in the embodiment depicted in FIG. 6a, microwave distribution system 514 can comprise at least two (e.g., two or more) pairs of oppositely disposed or opposed launchers. As used herein, the term "opposed launchers" refers to two or more launchers positioned on generally opposite sides of a microwave chamber. In one embodiment, the opposed launchers may be oppositely facing. As used herein with respect to opposed microwave launchers, the term "oppositely facing" shall denote launchers whose central launch axes are substantially aligned with one another. For simplicity, central launch axis 523c of launcher 522c and central launch axis 523d of launcher 522d are the only central launch axes illustrated in FIG. 6a. However, it should be understood that each of launchers 522a-f include a similar launch axes.

Opposed launchers may be generally aligned with one another, or may be staggered from one or more other launchers disposed on the opposite side of microwave chamber 520. In one embodiment, a pair of opposed launchers may be a staggered pair of launchers, such that the discharge openings 524 of the launchers 522 are not in substantial alignment with one another. Launchers 522a and 522e constitute one exemplary pair of opposed launchers arranged in a staggered configuration. Staggered opposed launchers may be axially or laterally staggered from one another. As used herein with respect to opposed microwave launchers, the term "axially staggered" shall denote launchers whose central launch axes are axially spaced from one another. As used herein with respect to opposed microwave launchers, the term "laterally staggered" shall denote launchers whose central launch axes are laterally spaced from one another. In another embodiment, a pair of opposed launchers may be directly opposite launchers, such that the discharge openings of the launcher pair are substantially aligned. For example, launchers 522c and 522d shown in FIG. 6a are configured as a pair of opposite launchers.

Figure 6B:
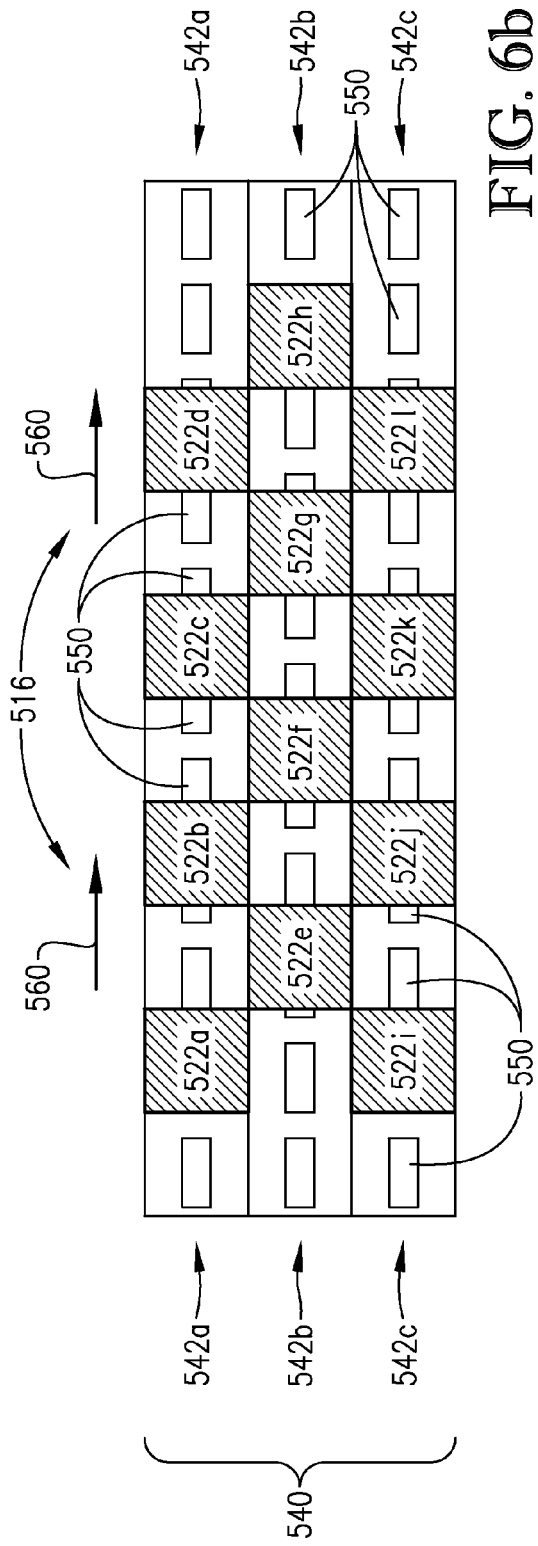
FIG. 6b is a schematic top view of a microwave heating zone configured according to one embodiment of the present invention, particularly illustrating one configuration of microwave launchers in a heating system employing a multi-line convey system.
Figure 6C:
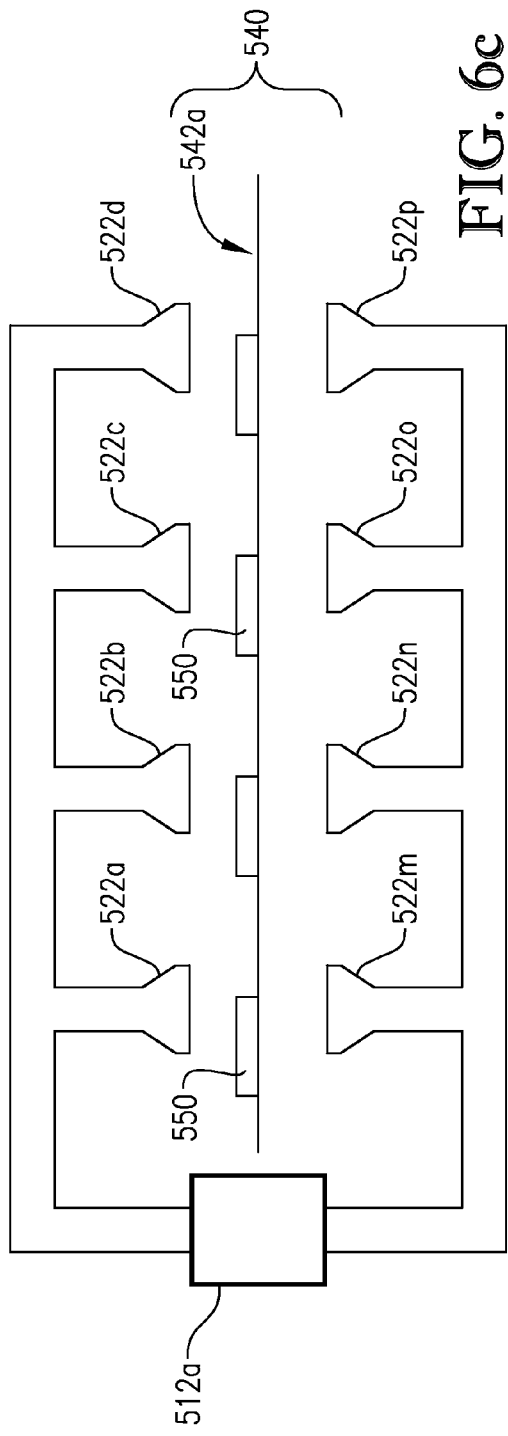
FIG. 6c is a schematic side view of the microwave heating zone illustrated in FIG. 6b, particularly showing the one set of microwave launchers configured to heat articles passing along a convey line.

In some embodiments, microwave heating zone 516 can include two or more convey lines operating simultaneously with one another. An exemplary multi-line conveyance system 540 is shown in FIGS. 6b and 6c. As shown in FIGS. 6b and 6c, conveyance system 540 can be configured to transport a plurality of articles 550 in a convey direction generally represented by arrow 560 in FIG. 6b. In one embodiment, conveyance system 540 can include at least two laterally spaced, substantially parallel convey lines, such as, for example, first, second, and third convey lines 542a-c shown in FIG. 6b. Convey lines 542a-c can, in one embodiment, comprise individual conveyance systems, while, in another embodiment, each of convey lines 542a-c can be portions of an overall conveyance system. Conveyance system 540 and/ or convey lines 542a-c can be any suitable type of conveyor or conveyance system, including those discussed in detail previously.

Microwave heating system 516 depicted in FIGS. 6b and 6c includes a plurality of microwave launchers 522 that can be divided or organized into at least two groups of two or more microwave launchers. Each of first, second, and third convey lines 542a-c can be configured to receive microwave energy from respective first, second, and third groups of microwave launchers. In one embodiment, a "group" of launchers can refer to two or more axially spaced launchers, generally position along the convey direction (e.g., launcher group 522a-d, launcher group 522e-h, and/or launcher group 522i-l shown in FIG. 6b), while, in the another embodiment, a "group" of launchers can include one or more pairs of opposed launchers positioned on different sides of a microwave chamber (e.g., groups that include pair of launchers 522a and 522m, the group that includes pair of launchers 522b and 522n, group that includes pair of launchers 522c and 522o, and group that includes pair of launchers 522d and 522p, as shown in FIG. 6c). When the group of launchers comprises one or more pairs of opposed launchers, the launchers can be arranged in a staggered configuration (not shown) or can be directly opposite one another (e.g. oppositely facing), as illustrated in FIG. 6c. According to one embodiment, at least one generator, shown as generator 512a in FIG. 6b, can be configured to provide microwave energy to at least one group of microwave launchers.

As particularly shown in FIG. 6b, individual microwave launchers 522 of adjacent convey lines 542 can be arranged in a staggered configuration relative to one another in the convey direction. In one embodiment, one or more same-side microwave launchers 522a-l may be axially staggered from one another. For example, in the embodiment shown in FIG. 6b, launchers 522a-d associated with first convey line 542a are arranged in a staggered configuration relative to each of respective launchers 522e-h associated with second convey line 542b with respect to and/or along the convey direction 560. As used herein with respect to same-side microwave launchers, the term "axially staggered" shall denote launchers that are axially spaced from one another by distance greater that ½ the maximum axial dimension of the launch openings of the launchers. As used herein with respect to same-side microwave launchers, the term "laterally staggered" shall denote launchers that are laterally spaced from one another by a distance greater that ½ the maximum lateral dimension of the launch openings of the launchers.

Additionally, in the same or another embodiment, the microwave launchers associated with the non-adjacent convey lines (e.g., first and third convey lines 542a,c) can be arranged in a substantially aligned configuration relative to one another, as illustrated by the arrangement of launchers 522a-d relative to launchers 522i-l shown in FIG. 6b. Alternatively, at least a portion of the launchers 522i-l associated with third convey line 542c may be staggered with respect to launchers 522a-d of first convey line 542a and/or second convey line 542b (embodiment not shown). Although generally depicted in FIG. 6b as including little to no space between launchers of adjacent convey lines, it should be understood that, in one embodiment, that some space may exist between launchers of adjacent lines (e.g., launchers 522a and 522e, launchers 522b and 522f, etc.). Further, individual launchers 522 can have any suitable design or configuration and, in one embodiment, can include at least one feature from one or more embodiments of the present invention which will be described in detail herein.

Figure 7A:
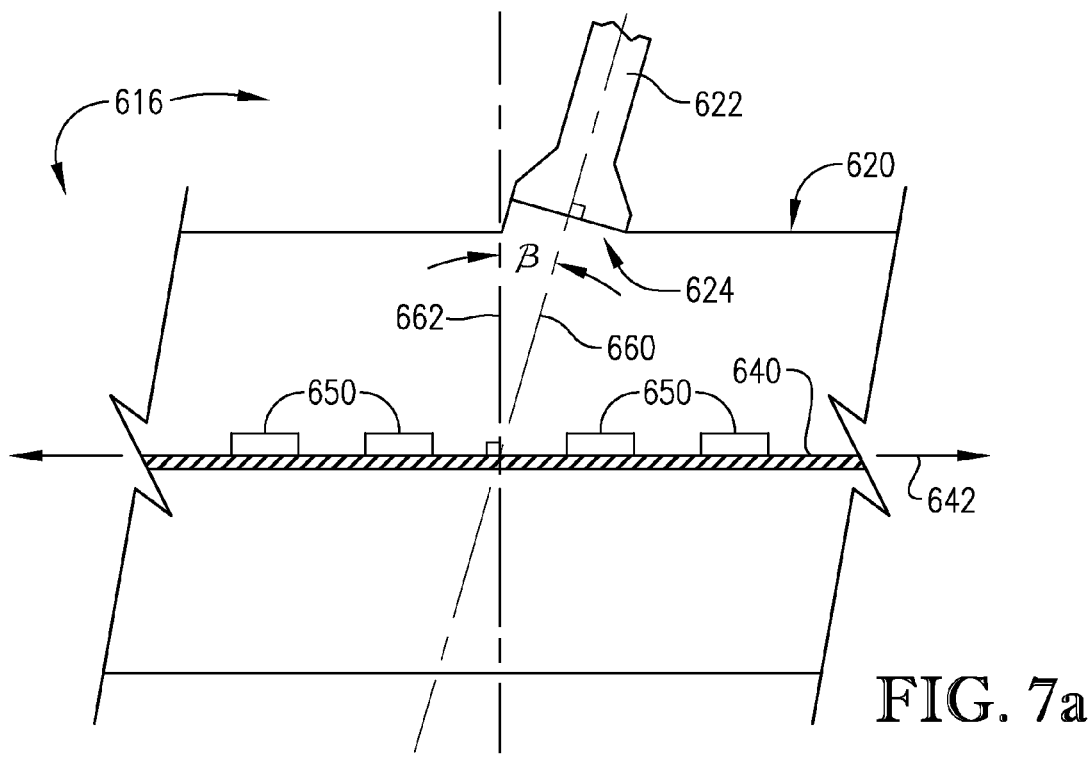
FIG. 7a is a partial side cut-away view of a microwave heating zone configured according to one embodiment of the present invention, particularly illustrating a titled microwave launcher and showing what is meant by the term "launch tilt angle" ($\beta$)

Turning now to FIG. 7a, a partial view of one embodiment of a microwave heating zone 616 is shown. Microwave heating zone 616 includes at least one microwave launcher 622 that defines a launch opening 624 for discharging energy into a microwave chamber 620. As shown in FIG. 7a, microwave launcher 622 is configured to discharge microwave energy along a central launch axis 660 toward a conveyance system 640 configured to transport a plurality of articles 650 within microwave chamber 620 along a convey axis 642. In one embodiment, central launch axis 660 can be tilted such that a launch tilt angle, β, is defined between central launch axis 660 and a plane normal to convey axis 642, illustrated as plane 662 in FIG. 7a. According to one embodiment, launch tilt angle β can be at least about 2°, at least about 4°, at least about 5° and/or not more than about 15°, not more than about 10°, or not more than about 8°.

Figure 7B:
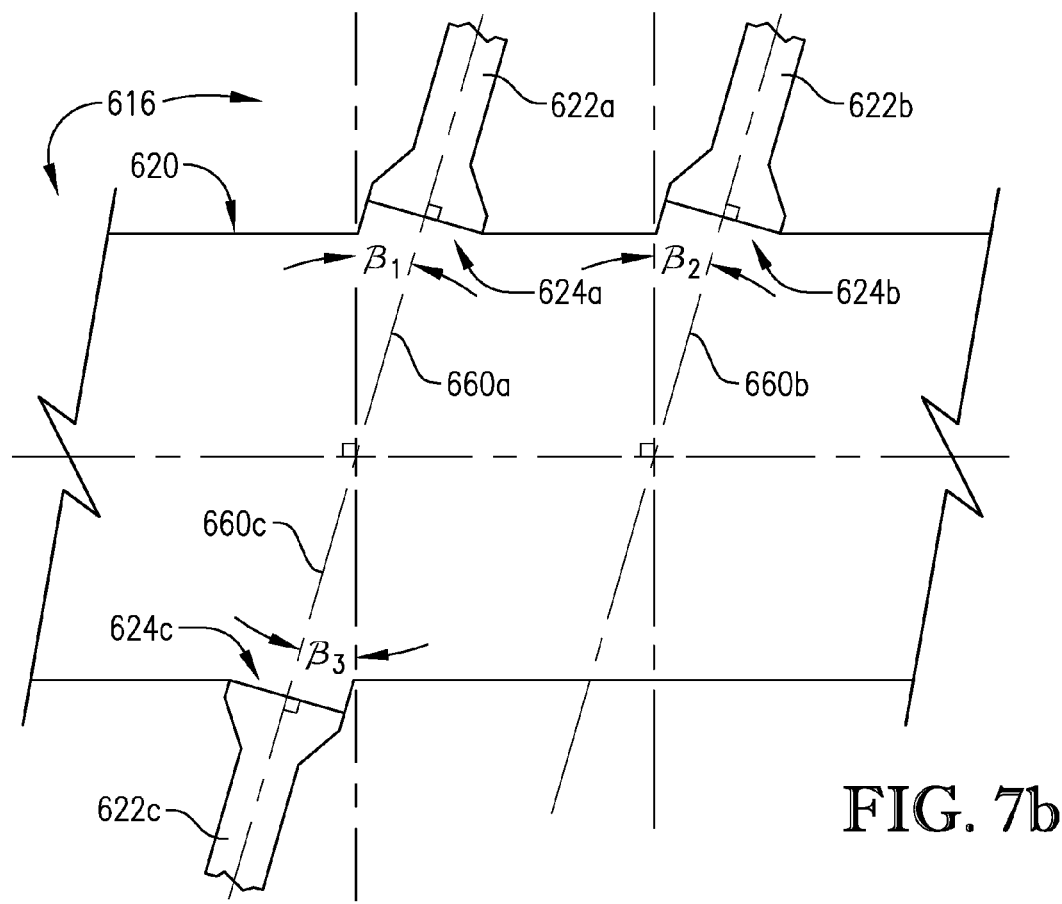
FIG. 7b is a partial side cut-away view of another embodiment of a microwave heating zone, particularly illustrating a microwave distribution system comprising a plurality of tilted launchers.

Turning now to FIG. 7b, another embodiment of a microwave heating system 616 is shown as including two or more launchers 622a-c, each configured to discharge energy into microwave chamber 620 along respective tilted central launch axes 660a-c. In one embodiment wherein microwave heating system 616 includes two or more tilted launchers, the central launch axes of the launchers, especially the same-side launchers, can be substantially parallel to one another, as generally illustrated by central launch axes 660a,b of launchers 622a,b shown in FIG. 7b. As used herein, the term "substantially parallel" means within 5° of being parallel. In the same or another embodiment, the central launch axes of two or more launchers, especially opposed launchers, within microwave heating zone 616 can be substantially parallel or substantially aligned, as illustrated by launch axes 660a,c of microwave launchers 622a,c in FIG. 7b. When microwave heating zone 616 comprises n tilted microwave launchers having central launch axes oriented as described above, each launcher can define a respective launch tilt angle, $\beta_n$, within the ranges discussed previously. In one embodiment, each of the launch tilt angles $\beta_n$ of each launcher may be substantially the same, while, in another embodiment, at least one of the launch tilt angles $\beta_n$ can be substantially different than one or more other launch tilt angles.

Referring back to FIG. 6a, at least one of launch openings 524a-f of launchers 522a-f of microwave system 516 can be at least partially covered by a substantially microwave-transparent window 526a-f disposed between each launch opening 524a-f and microwave chamber 520. Microwave-transparent windows 526a-f can be operable to prevent fluid flow between microwave chamber 520 and microwave launchers 522a-f while still permitting a substantial portion of the microwave energy from launchers 522a-f to pass therethrough. Windows 526a-f can be made of any suitable material, including, but not limited to one or more thermoplastic or glass material such as glass-filled Teflon, polytetrafluoroethylene (PTFE), poly(methyl methacrylate) (PMMA), polyetherimide (PEI), aluminum oxide, glass, and combinations thereof. In one embodiment, windows 526a-f can have an average thickness of at least about 4 mm, at least about 6 mm, at least about 8 mm and/or not more than about 20 mm, not more than about 16 mm, or not more than about 12 mm and can withstand a pressure difference of at least about 40 psi, at least about 50 psi, at least about 75 psi and/or not more than about 200 psi, not more than about 150 psi, or not more than about 120 psi without breaking, cracking, or otherwise failing.

Figure 8A:
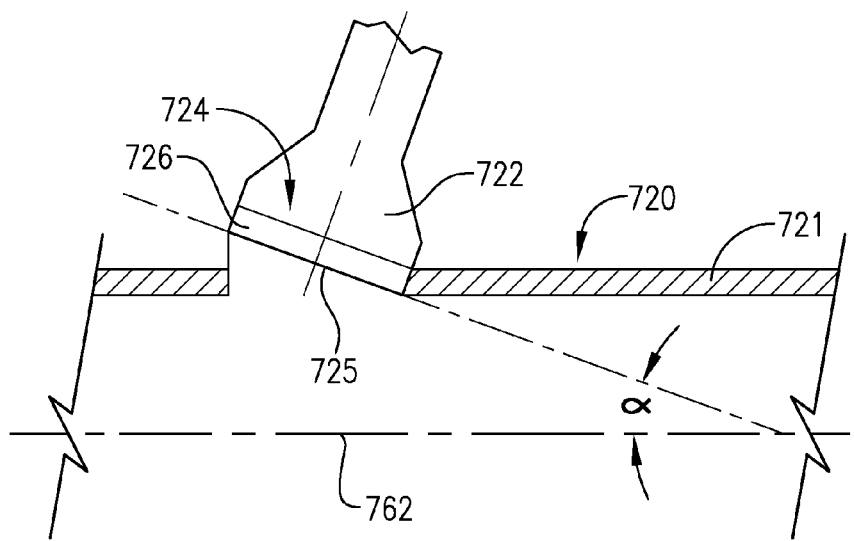
FIG. 8a is a partial enlarged side cut-away view of a portion of a microwave heating zone, particularly illustrating one embodiment of a microwave window located near the discharge opening of at least one microwave launcher of the heating zone.
Figure 8B:
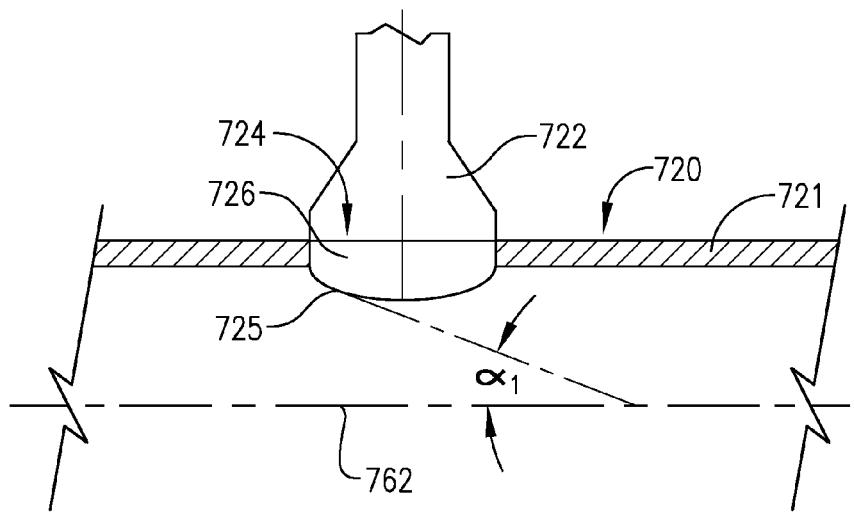
FIG. 8b is a partial enlarged side cut-away view of a portion of a microwave heating zone, particularly illustrating another embodiment of a microwave window located near the discharge opening of at least one microwave launcher of the heating zone.
Figure 8C:
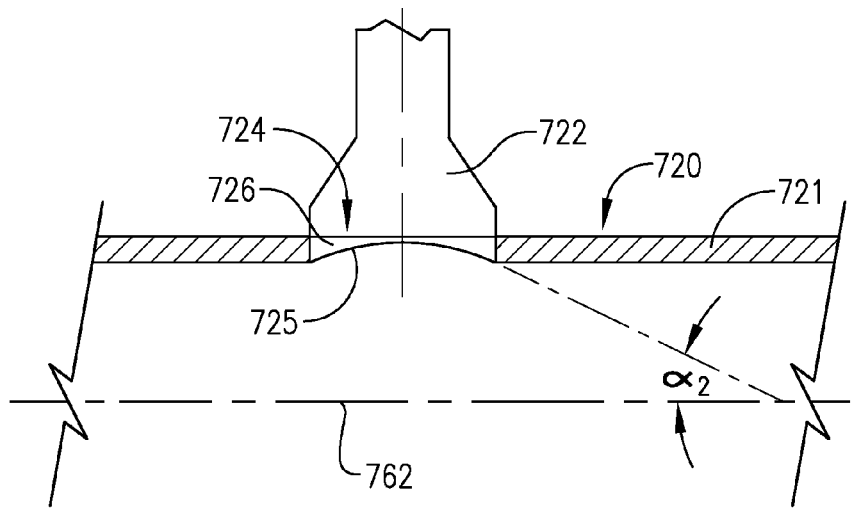
FIG. 8c is a partial enlarged side cut-away view of a portion of a microwave heating zone, particularly illustrating yet another embodiment of a microwave window located near the discharge opening of at least one microwave launcher of the heating zone.

Several embodiments of suitable configurations for microwave launcher windows are generally depicted in FIGS. 8a-c. As shown in FIGS. 8a-c, each of microwave windows 726 define a chamber-side surface 725 that can optionally define at least a portion of the sidewall 721 of microwave chamber

720. According to one embodiment shown in FIG. 1, chamber-side surface 725 of window 726 can be configured such that at least about 50 percent, at least about 65 percent, at least about 75 percent, at least about 85 percent, or at least about 95 percent of the total surface area of chamber-side surface 725 is oriented at a tilt angle, a, from the horizontal. Tilt angle α can be at least about 2°, at least about 4°, at least about 8°, at least about 10° and/or not more than about 45°, not more than about 30°, or not more than about 15° from the horizontal, illustrated as dashed line 762. In other embodiments, the tilt angle, a, may also be defined between the axis of elongation 762 of microwave chamber 720 and/or an axis of convey (not shown in FIGS. 8a-c) when, for example, these axes are parallel to the horizontal.

Chamber-side surface 725 of window 726 can be oriented from the horizontal regardless of whether or not launcher 722 is oriented with a launch tilt angle as described above. In one embodiment, window 726 can be substantially planar and sloped from the horizontal (as shown in FIG. 8a), while, in the same or another embodiment, chamber-side surface 725 of window 726 can include one or more convexities (as shown in FIG. 8b) or concavities (as shown in FIG. 8c). When chamber-side surface 725 is not substantially planar, one or more (or n) total tilt angles may be formed as described above. Depending on the exact configuration of chamber-side surface 725, the multiple tilt angles formed thereby may be the same as or different than other tilt angles formed by the same surface 725.

Figure 9C:
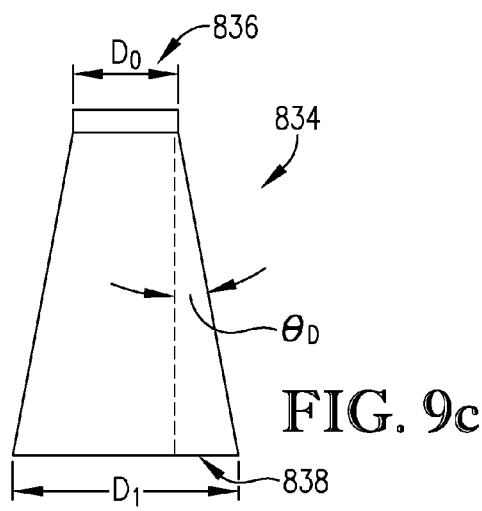
FIG. 9c is an end view of the microwave launcher depicted in FIGS. 9a and 9b, particularly illustrating a launcher having a flared outlet.

As discussed previously, the microwave launchers 522a-f depicted in FIG. 6a may be of any suitable configuration. Several views of a microwave launcher 822 configured according to one embodiment of the present invention are provided in FIGS. 9a-f. Referring initially to FIG. 9a, microwave launcher 822 is illustrated as comprising a set of opposing sidewalls 832a,b and a set of opposing end walls 834a,b, which collectively define a substantially rectangular launch opening 838. When launch opening 838 comprises a rectangular-shaped opening, it can have a width ($W_1$) and a depth ($D_1$) defined, at least in part, by the terminal edges of sidewalls 832a,b and 834a,b, respectively. In one embodiment, sidewalls 832a,b can be broader than end walls 834a,b such that the length of the lower terminal edge of sidewalls 832a,b, shown as $W_1$ in FIG. 9a, can be greater than the length of the lower terminal edge of end walls 834a,b, depicted in FIG. 9a with the identifier $D_1$. As shown in FIG. 9a, the elongated portion of side walls 832a,b and end walls 834a,b can also collectively define a pathway 837 through which microwave energy can propagate as it passes from the microwave inlet 836 to the at least one launch opening 838 defined by launcher 822.

When used to discharge microwave energy into a microwave chamber, launch opening 838 can be can be elongated in the direction of extension of the microwave chamber (not shown) or in the direction of convey of the articles therein. For example, in one embodiment, side walls 832a,b and end walls 834a,b of launcher 822 can be configured such that the maximum dimension of launch opening 838 (shown in FIG. 9a as $W_1$) can be aligned substantially parallel to the direction of extension of the microwave chamber and/or to the direction of convey of articles passing therethrough. In this embodiment, the terminal edges of side walls 832a,b can be oriented parallel to the direction of extension (or the direction of convey), while the terminal edges of end walls 834a,b may be aligned substantially perpendicular to the direction of extension or convey within the microwave chamber (not shown in FIG. 9).

FIGS. 9b and 9c respectively provide views of a sidewall 832 and end wall 834 of microwave launcher 822 illustrated in FIG. 9a. It should be understood that, while only one of the side or end walls 832, 834 are shown in FIGS. 9b and 9c, the other of the pair could have a similar configuration. In one embodiment, at least one of side wall 832 and end wall 834 can be flared such that the inlet dimension (width $W_0$ or depth $D_0$) is smaller than the outlet dimension (width $W_1$ or depth $D_1$), as respectively illustrated in FIGS. 9b and 9c. When flared, each of side and end walls 832, 834 define respective width and depth flare angles, $\theta_w$ and $\theta_d$, as shown in FIGS. 9b and 9c. In one embodiment, width and/or depth flare angles $\theta_w$ and/or $\theta_d$ can be at least about 2°, at least about 5°, at least about 10°, or at least about 15° and/or not more than about 45°, not more than about 30°, or not more than about 15°. In one embodiment, the width and depth flare angles $\theta_w$ and $\theta_d$ can be the same, while, in another embodiment, the values for $\theta_w$ and $\theta_d$ may be different.

Figure 9E:
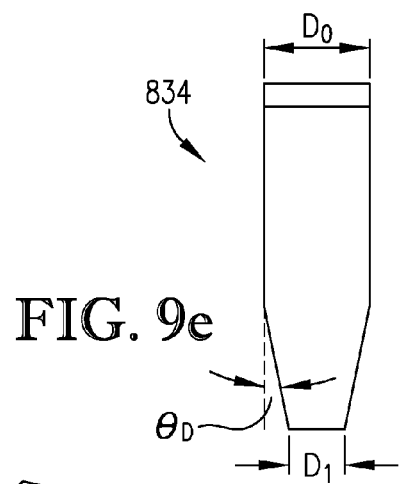
FIG. 9e is an end view of yet another embodiment of the microwave launchers generally depicted in FIGS. 9a and 9b, particularly illustrating a launcher having a tapered outlet.
Figure 9D:
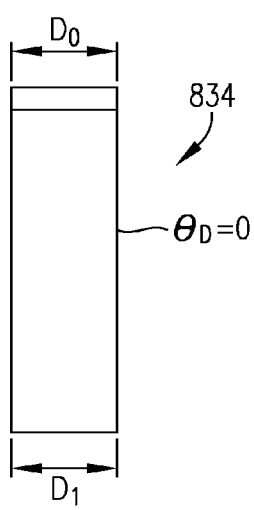
FIG. 9d is an end view of another embodiment of the microwave launcher generally depicted in FIGS. 9a and 9b, particularly illustrating a launcher having an inlet and outlet of approximately the same size.

According to one embodiment, depth flare angle $\theta_d$ can be smaller than width flare angle $\theta_w$. In certain embodiments, depth flare angle $\theta_d$ can be not more than about 0°, such that the inlet depth $D_0$ and the outlet dimension $D_1$ of microwave launcher 822 are substantially the same, as illustrated in the embodiment depicted in FIG. 9d. In another embodiment, the depth flare angle $\theta_d$ may be less than 0°, such that $D_1$ is smaller than $D_0$, as shown in FIG. 9e. When microwave launcher 822 comprises a depth flare angle less than 0° and/or the depth $D_1$ of launch opening 838 is smaller than the depth $D_0$ of microwave inlet 836, microwave launcher 822 can be a tapered launcher having a generally inverse profile. In one embodiment wherein microwave launcher 822 comprises n launch openings, between 1 and n of the openings can have a depth and/or width less than or equal to the depth and/or width of the inlet of the launcher. Further embodiments of multi-opening launchers will be discussed in detail below.

According to one embodiment of the present invention, the depth $D_1$ of launch opening 838 can be no more than about 0.625λ, not more than about 0.5λ, not more than about 0.4λ, not more than about 0.35λ, or not more than about 0.25λ, wherein λ is the wavelength of the predominant mode of microwave energy discharged from launch opening 838. Although not wishing to be bound by theory, it is believed that minimizing the depth $D_1$ of launch opening 838, the microwave field created proximate launch opening 838 is more stable and uniform than would be created by launchers having greater depths. In one embodiment wherein microwave launcher 822 comprises n launch openings, the depth of each launch opening, $d_n$, can be not more than about 0.625λ, not more than about 0.5λ, not more than about 0.4λ, not more than about 0.35λ, or not more than about 0.25λ. When microwave launcher 822 has multiple openings, each opening can have a depth that is the same or different than one or more of the other launch openings of the same launcher.

Figure 10A:
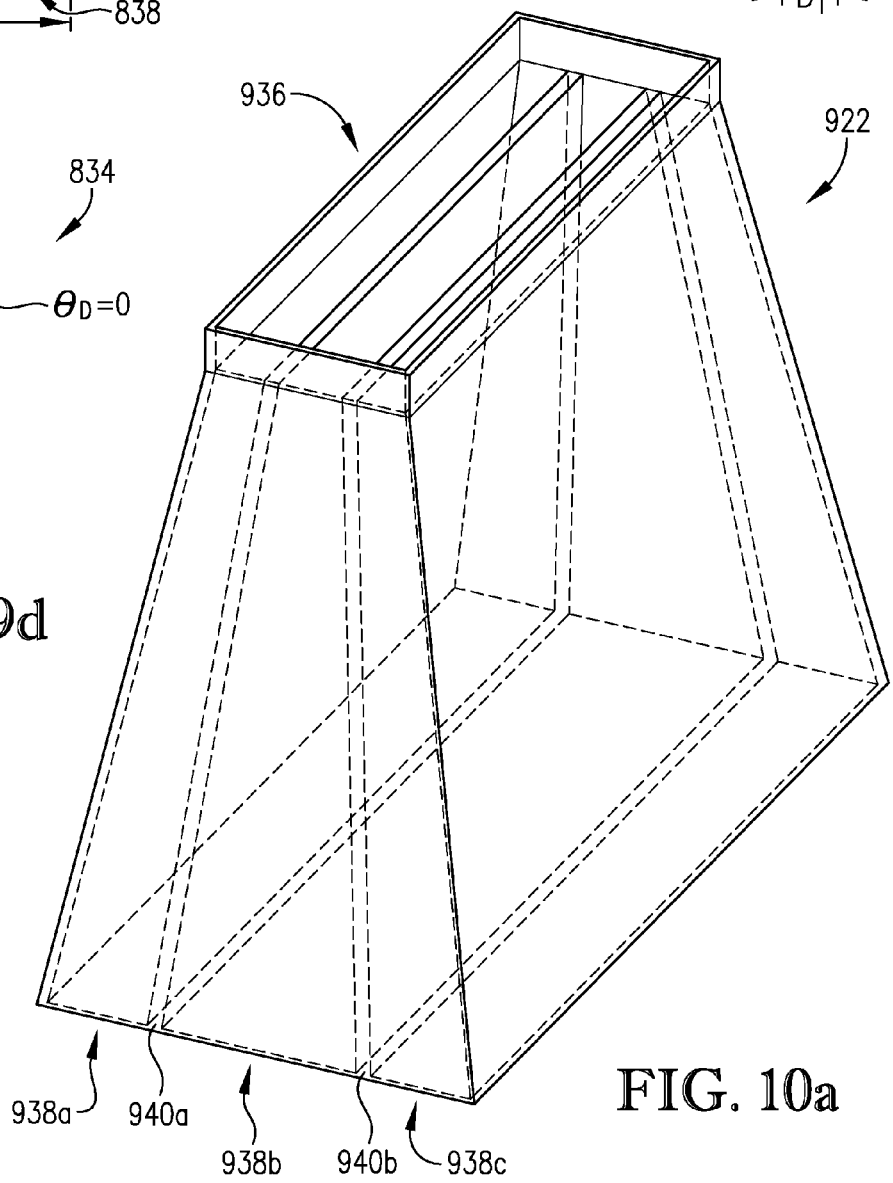
FIG. 10a is an isometric view of another microwave launcher configured according to one embodiment of the present invention, particularly illustrating a launcher comprising a single microwave inlet and a plurality of microwave outlets.

Referring now to FIGS. 10a-c, another embodiment of a microwave launcher 922 suitable for use in the microwave heating systems described herein is illustrated as comprising a single microwave inlet 936 and two or more launch openings, shown as launch or discharge openings 938a-c, for discharging microwave energy therefrom. Microwave launcher 922 illustrated in FIGS. 10a-c includes first, second, and third spaced apart launch openings 938a-c, which are laterally spaced from one another. Although described herein as defining three launch openings, it should be understood that launcher 922 can include any suitable number of launch openings including at least 2, at least 3, at least 4 and/or not more than 10, not more than 8, or not more than 6. The spacing between each of first, second, and third launch openings 938a-c can be at least about 0.05λ, at least about 0.075λ, or at least about 0.10λ and/or not more than about 0.25λ, not more than about 0.15λ, or not more than about 0.1λ, wherein λ is the wavelength of the predominant mode of microwave energy discharged from launcher 922.

In one embodiment, each of first, second, and third launch openings are separated by one or more dividing septum (or septa) 940a,b disposed within the interior of launcher 922, as shown in FIGS. 10a-c. Septa 940a,b typically have a thickness equal to the desired spacing between the discharge openings 938a-c. When microwave launcher comprises n septa, microwave launcher 922 defines (n+1) separated launch openings and (n+1) separate microwave pathways 937a-c defined between microwave inlet 836 and each of launch openings 938a-c, as particularly shown in FIG. 10c. As shown in FIG. 10c, each of microwave pathways 937a-c has a length, $L_1$-$L_3$, which extends from inlet 936 to a point perpendicular with respective launch opening 938a-c. Each of $L_1$-$L_3$ can be substantially the same, or at least one of $L_1$, $L_2$, and $L_3$ can be substantially different. According to one embodiment, particularly shown in FIG. 10c, one or more pathways 937a-c can be longer than one or more other pathways 937a-c.

When one or more pathways 937a-c are of different lengths than one or more other pathways, the dimensions ($L_1$, $L_2$, and/or $L_3$) of pathways 937a-c may be adjusted such that the phase velocity of the microwave energy propagating therethrough accelerates at a more rapid pace within the longer microwave pathways (e.g., $L_1$ and $L_3$ in FIG. 10c) than through the shorter pathways (e.g., $L_2$ in FIG. 10c). Although not wishing to be bound by theory, it is hypothesized that such adjusting can be carried out to ensure uniform synchronization of individual wave portions, thereby creating a uniform wave front as the microwave energy is discharged into chamber 520. When microwave launcher 922 includes a single septum, only two microwave pathways are created (embodiment not shown) and the length of each pathway is substantially the same. Consequently, little or no control of the phase velocity of microwave energy passing through the equal length pathways may be needed.

In the same or another embodiment, each of launch openings 938a-c can define a depth, $d_{1-3}$, as generally depicted in FIG. 10b. In one embodiment, each of depths $d_1$ through $d_3$ can be substantially the same, while, in another embodiment, at least one of the depths $d_1$-$d_3$ can be different. As discussed previously, one or more of $d_1$-$d_3$ can be not more than about 0.625λ, not more than about 0.5λ, not more than about 0.4λ, not more than about 0.35λ, or not more than about 0.25λ, wherein λ is the wavelength of the predominant mode of microwave energy discharged from launch opening 938a-c. In addition, in one embodiment, at least one of $d_1$-$d_3$ can be less than or equal to the depth $d_0$ of inlet 936 as discussed in detail previously. As shown in FIG. 10b, the depths, $d_{1-3}$, of each of launch openings 938a-c do not include the thickness of septa 940a,b, when present.

Referring again to FIG. 6a, in one embodiment, the microwave distribution system 514 of microwave heating zone 516 can include at least one microwave distribution manifold 525a,b for allocating or distributing microwave energy into chamber 520 via a plurality of launchers 522a-c and 522d-f. In one embodiment, microwave distribution manifold 525a,b can include at least three microwave allocation devices configured to divide the microwave energy from generator 512 into two or more separate portions prior to being discharged from at least some of microwave launchers 522a-f. As used herein, the term "microwave allocation device" refers to any device or item operable to divide microwave energy into two or more separate portions, according to a predetermined ratio. As used herein, the term "predetermined power ratio" refers to the ratio of the amount of power of each resultant separate portion exiting a specific microwave allocation device. For example, a microwave allocation device configured to divide the power passing therethrough at a 1:1 power ratio would be configured to divide the power introduced therein into two substantially equal portions.

However, in one embodiment of the present invention, at least one of the microwave allocation devices, shown as inductive irises 570a-h and "T-shaped" or two-way splitter 572 in FIG. 6a, of microwave distribution system 514 can be configured to have a predetermined power ratio that is not 1:1. For example, one or more of the microwave allocation devices 570a-h or 572 can be configured to divide the microwave energy passing therethrough according to a predetermined power ratio of at least about 1:1.5, at least about 1:2, at least about 1:3 and/or not more than about 1:10, not more than about 1:8, or not more than about 1:6.

Each of the allocation devices 570a2-h and/or 5 employed by microwave distribution system 514 may be configured to discharge energy according to the same ratio, or one or more of allocation devices 570a-h can be configured at a different power ratio. Allocation devices 570a-h and 572 can be configured such that substantially the same amount of power is discharged from each of launchers 522a-f, while, in another embodiment, the allocation devices 570a-h and 572 can be collectively designed such that more power is diverted to and discharged from one or more launchers 522a-f, with less power being discharged through the remainder of the launchers 522a-f. The specific power ratios utilized each of microwave allocation devices 570a-h and 572, as well as the pattern or overall configuration of microwave energy allocation within the system, can depend on a variety of factors including, for example, the type of articles being heated, the desired operating conditions of the microwave heating zone 516, and other similar factors.

In operation, an initial quantity of microwave power can be introduced into microwave distribution system 514 and can be divided into two portions as it passes through splitter 572. In one embodiment, the two portions of microwave energy exiting splitter 572 can be approximately of approximately the same power, while, in another embodiment, one of the two portions may have more power than the other. As shown in FIG. 6a, each portion may pass to a respective manifold 525a,b, optionally passing through a phase shifting device 530 prior to entering manifold 525a,b. Described now with respect to microwave distribution manifold 525a, it should be understood that analogous operation is applicable to the lower manifold 525b shown in FIG. 6a.

The microwave power exiting splitter 572 and optionally phase shifting device 530 (embodiments of which will be discussed in detail below) may then pass through a microwave allocation device, shown as iris 570a, whereupon the power can be divided into a first launch microwave fraction and a first distribution microwave fraction. The first launch microwave fraction can be directed toward launcher 522a and can be discharged via outlet 524a The first distribution microwave fraction can be propagated down waveguide 518 toward the additional microwave launchers 522b,c. According to one embodiment, the power ratio of the first launch microwave fraction to the first distribution microwave fraction exiting iris 570a can be not more than about 1:1, not more than about 0.95:1, not more than about 0.90:1, not more than 0.80:1, not more than about 0.70:1 or not more than 0.60:1. In one embodiment, the power ratio of the first launch microwave fraction to the first distribution microwave fraction is not 1:1.

As the first distribution microwave fraction propagates toward launchers 522b,c, it can subsequently be divided into a second launch microwave fraction directed toward launcher 522b to be discharged via launch outlet 524b, and a second distribution microwave fraction that propagates down waveguide 518 toward launcher 522c. In one embodiment, the ratio of second launch microwave fraction to second distribution microwave fraction can be at least about 0.80:1, at least about 0.90:1, at least about 0.95:1 and/or not more than about 1.2:1, not more than about 1.1:1, not more than about 1.05:1, or can be approximately 1:1. Subsequently, the remainder of the microwave energy (e.g., the entirety of the second distribution microwave fraction) can then be directed to the final microwave launcher 522c and discharged from launch outlet 524c.

According to another embodiment (not shown in FIG. 6a), microwave distribution system 514 can include a microwave distribution manifold 525a,b having more than three launchers. For example, when microwave distribution manifold 525 includes n launchers, all but the (n−1)th step of dividing can be carried out such that the ratio of the launch microwave fraction to the distribution microwave fraction is not 1:1. For each of the steps except the (n−1)th step, the power ratio can be not more than about 1:1, not more than about 0.95:1, not more than about 0.90:1, not more than about 0.80:1, not more than about 0.70:1 or not more than 0.60:1, while the (n−1)th dividing step can be carried out such that the ratio of the launch microwave fraction to second distribution microwave fraction can be at least about 0.80:1, at least about 0.90:1, at least about 0.95:1 and/or not more than about 1.2:1, not more than about 1.1:1, not more than about 1.05:1, or can be approximately 1:1. The (n−1)th distribution microwave fraction can then be sent, in its majority or entirety, as an nth launch microwave fraction to be discharged to the microwave chamber via the nth microwave launcher.

In addition to one or more irises 570a-h positioned within microwave distribution system 514, one or more of launchers 522 can also include at least one inductive iris disposed within the launcher, as shown in one embodiment illustrated in FIGS. 11a and 11b. Alternatively, one or more of irises 570b and/or 570d may be disposed within launchers 522a and/or 522b, respectively, rather than be disposed within a waveguide as shown in FIG. 6a.

One embodiment of a microwave launcher 1022 including an inductive iris disposed therein is shown in FIG. 11a. Launcher 1022 may include at least one inductive iris 1070 located between its microwave inlet 1036 and one or more launch openings 1038, as generally illustrated in FIGS. 11a and 11b. As shown in FIGS. 11a and 11b, iris 1070 may be defined by a pair of inductive iris panels 1072a,b disposed on opposite sides of launcher 1022. Although illustrated as being coupled to narrower opposing end walls 1034a,b of launcher 1022, it should be understood that first and second iris panels 1072a,b could also be coupled to broader opposing side walls 1032a,b of launcher 1022. As shown in FIGS. 11a and 11b, first and second iris panels 1072a,b extend inwardly into the microwave pathway 1037 defined between microwave inlet 1036 and launch opening 1038 in a direction that is generally transverse to the direction of microwave propagation through pathway 1037. In one embodiment, iris panels obstruct at least about 25 percent, at least about 40 percent, or at least about 50 percent and/or not more than about 75 percent, not more than about 60 percent, or not more than about 55 percent of the total area of microwave pathway 1037 at the location at which they are disposed. When microwave launcher 1022 comprises two or more launch openings, as shown in FIG. 11c, first and second iris panels 1072a,b can be configured to obstruct at least a portion of each of the launch openings 1038a-c of the launcher 1022.

As shown in FIG. 11a, first and second iris panels 1072a,b can be substantially co-planar and can be oriented substantially normal to the central launch axis of microwave launcher 1022. In certain embodiments, the iris panels 1072a,b may be spaced from both the microwave inlet 1036 and the launch opening 1038 of microwave launcher 1022. For example, the iris panels 1072a,b can be spaced from microwave inlet 1036 of launcher 1022 by at least about 10 percent, at least about 25 percent, or at least about 35 percent of the minimum distance between microwave inlet 1036 and launch opening 1038 of launcher 1022. Further, iris panels 1072a,b can be spaced from launch opening 1038 of launcher 1022 by at least about 10 percent, 25 percent, or 35 percent of the maximum distance (L) measured between microwave inlet 1036 and launch opening 1038 of launcher 1022.

Turning again to FIG. 6a, microwave distribution system 514 is illustrated as further comprise one or more devices or for increasing the uniformity and/or strength of the microwave field created within microwave heating chamber 520. For example, in one embodiment, microwave distribution system 514 can include one or more devices designed to modify and/or control the location and strength of the constructive interference bands of the microwave field created within each of individual heating zones 580a-c, which are respectively defined between pairs of launchers 522a and 522f, 522b and 522e, and 522c and 522d. In one embodiment, such a device can be a phase shifting device, schematically represented in FIG. 6a as device 530, operable to cyclically shift the phase of the microwave energy passing therethrough.

As the articles 550 move along conveyance system 540 within microwave chamber 520, each article 550 can have an average residence time (τ), within each individual heating zone 580a-c, of at least about 2 seconds, at least about 10 seconds, at least about 15 seconds and/or not more than about 1 minute, not more than about 45 seconds, or not more than about 30 seconds. In one embodiment, the average residence time (τ) for articles 550 can be greater than the phase shifting rate (t) for which phase shifting device 530 is configured. For example, the ratio of the average residence time of the articles passing through one of individual heating zones 580a-c to the phase shifting rate of device 530 (τ:t) can be at least about 2:1, at least about 3:1, at least about 4:1, at least about 5:1 and/or not more than about 12:1, not more than about 10:1, or not more than about 8:1.

Phase shifting device 530 can be any suitable device for rapidly and cyclically shifting the phase of microwave energy passing through microwave distribution system 514. According to one embodiment, phase shifting device 530 can be configured to shift the microwave energy passing therethrough at a phase shifting rate (t) of at least about 1.5 cycles per second, at least about 1.75 cycles per second, or at least about 2.0 cycles per second and/or not more than about 10 cycles per second, not more than about 8 cycles per second, and/or not more than about 6 cycles per second. As used herein, the term "phase shifting rate" refers to the number of complete phase shift cycles completed per second. A "complete phase shift cycle" refers to a phase shift from 0° to 180° and back to 0°. Although shown as including a single phase shifting device 530, it should be understood that any suitable number of phase shifting devices can be utilized within microwave distribution system 514.

In one embodiment, phase shifting device 530 can comprise a plunger-type tuning device operable to be moved in a generally linear (e.g., up-and-down motion) within a cylinder to thereby cause the phase of the microwave energy passing therethrough to be cyclically shifted. FIGS. 12a and 12b illustrate two embodiments of a plunger-type tuning device 1130a,b suitable for use in microwave distribution system 514. FIG. 12a depicts a single-plunger phase shifting device 1130a that includes one plunger 1132 operable to move within a single cylinder 1134 via an automatic driver 1136. FIG. 12b illustrates another embodiment of a phase shifting device that comprises a multi-plunger phase shifting device that includes a plurality of plungers 1132a-d disposed and operable to moved within several corresponding cylinders 1134a-d. Plungers 1132a-d can be driven by a single automatic driver 1136, which can be connected to each of plungers 1132a-d via a rotatable cam shaft 1138. Either of plunger-type tuning devices 1130a,b can be connected to a coupler, such as, for example, a short slot hybrid coupler (not shown in FIGS. 12a and 12b) and can be employed in microwave distribution system 514 as a phase shifting device 530 as described above.

Another embodiment of a suitable phase shifting device is depicted in FIGS. 13a-e. In contrast to the phase shifting or tuning devices illustrated in FIGS. 12a and 12b, the phase shifting devices illustrated in FIGS. 13a-e are rotatable phase shifting devices. For example, as shown in FIGS. 13a-c, one embodiment of a rotatable phase shifting device 1230, also referred to as a variable phase short circuit, can comprise a fixed section 1210 defining a first substantially rectangular opening 1212 and a rotatable section 1240 positioned proximate said first opening 1212. As shown in FIG. 13a, a gap 1213 can be defined between rotatable section 1240 and fixed section 1210 and, in one embodiment, a microwave choke (not shown) can be at least partially disposed within gap 1213 for preventing the leakage of microwave energy from fixed and rotatable sections 1210 and 1240.

Rotatable section 1240 comprises a housing 1242 and a plurality of spaced apart, substantially parallel plates 1244a-d received within housing 1242. As shown in FIG. 13a, housing 1242 comprises a first end 1243a and a second end 1243b and first end 1243a defines a second opening 1246 adjacent to first rectangular opening 1212 of fixed section 1210. As indicated by arrows 1290, 1292 in FIG. 13a, rotatable section 1240 can be configured to be rotated relative to fixed section 1210 about an axis of rotation 1211 extending through first and second openings 1212, 1246, as generally shown in FIGS. 13a-c.

As particularly shown in FIGS. 13b and 13c, housing 1242 has a length ($L_H$), a width ($W_H$), and a depth ($D_H$). In one embodiment, at least one of $L_H$, $W_H$, and $D_H$ are at least about 0.5λ, at least about 0.65λ, at least about 0.75λ and/or not more than about 1 Å, not more than about 0.9λ, or not more than about 0.75λ, wherein λ is the wavelength of the microwave energy which variable phase short circuit 1230 is configured to pass between first and second openings 1212 and 1246. In one embodiment, at least one of $W_H$ and $D_H$ are at least about 0.5λ and both are not more than about λ. As generally shown in FIGS. 13a-c, the cross-sectional shape of housing 1242 is substantially square, such that the ratio of $W_H:D_H$ is not more than about 1.5:1, not more than about 1.25:1, or not more than about 1.1:1.

Fixed section 1210 can be any suitable shape or size and may comprise a circular or a rectangular waveguide. In one embodiment shown in FIG. 13d, first substantially rectangular opening 1212 can have a width ($W_R$) and a depth ($D_R$) such that the ratio of $W_R:D_R$ is at least about 1.1:1, at least about 1.25:1, or at least about 1.5:1. The width of first openings 1212 of fixed section 1210 and the width of second opening 1246 of rotatable section 1240 are substantially the same, such that the ratio $W_H:W_R$ is at least about 0.85:1, at least about 0.95:1, or at least about 0.98:1 and/or not more than about 1.15:1, not more than about 1.05:1, or not more than about 1.01:1.

As generally shown in FIG. 13a, each of plates 1244a-d can be coupled to second end 1243b of housing 1242 and can extend generally toward first end 1243a of housing 1242 in a direction toward first and second openings 1212 and 1244. Each of plates 1244a-d can have an extension distance or length, shown as $L_e$ in FIG. 13b, of at least about 0.1λ, at least about 0.2λ, at least about 0.25λ and/or not more than about 0.5λ, not more than about 0.35λ, or not more than about 0.30λ. Additionally, as particularly shown in FIG. 13c, one or more of plates 1244a-d can have a thickness, k, of at least about 0.01λ, at least about 0.05λ and/or not more than about 0.10λ, or not more than about 0.075λ, wherein λ is the wavelength of the microwave energy introduced into housing 1242 via first opening 1212. Adjacent plates 1244a-d can be spaced apart by a spacing distance, j, which can be greater than, approximately the same as, or less than the thickness of each plate. In one embodiment, j can be at least about 0.01λ, at least about 0.05λ and/or not more than about 0.10λ, or not more than about 0.075λ. Thus, in one embodiment, the ratio of the cumulative surface area of the distal ends of plates 1244a-d, generally illustrated as the shaded regions in FIG. 13c, to the total internal exposed surface area of second end 1243b of housing 1242, generally illustrated as the unshaded regions in FIG. 13c, can be at least about 0.85:1, at least about 0.95:1, or at least about 0.98:1 and/or not more than about 1.15:1, not more than about 1.10:1, or not more than about 1.05:1.

Variable phase short circuit 1230 can be configured to rotate at a speed of at least about 50 revolutions per minute (rpm), at least about 100 rpm, at least about 150 rpm and/or not more than about 1000 rpm, not more than about 900 rpm, or not more than about 800 rpm about axis of rotation 1211, as illustrated in FIG. 13a. In one embodiment, at least a portion of the movement of rotatable variable phase short circuit 1230 can be carried out via an actuator 1270 coupled to an automatic driver and/or automatic control system (not shown). In another embodiment, at least a portion of the movement can be carried out manually and may optionally include periods of non-rotation.

Figure 13F:
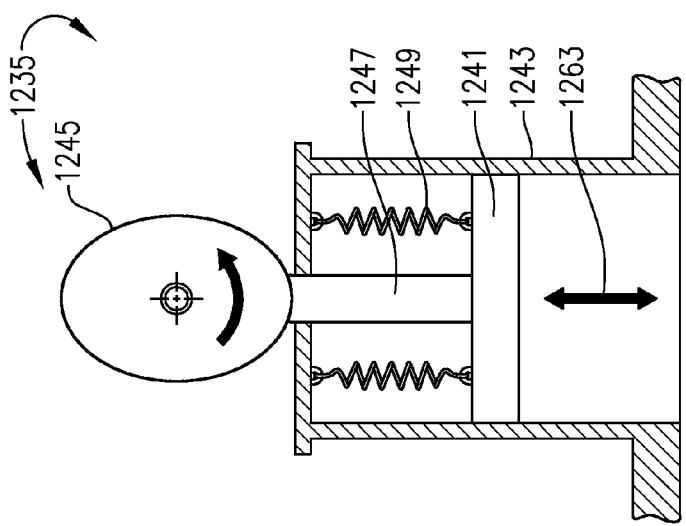
FIG. 13f is a side cut-away view of a rotatable phase shifting device configured according to yet another embodiment of the present invention, particularly illustrating a drive system that includes a set of compression springs.
Figure 13E:
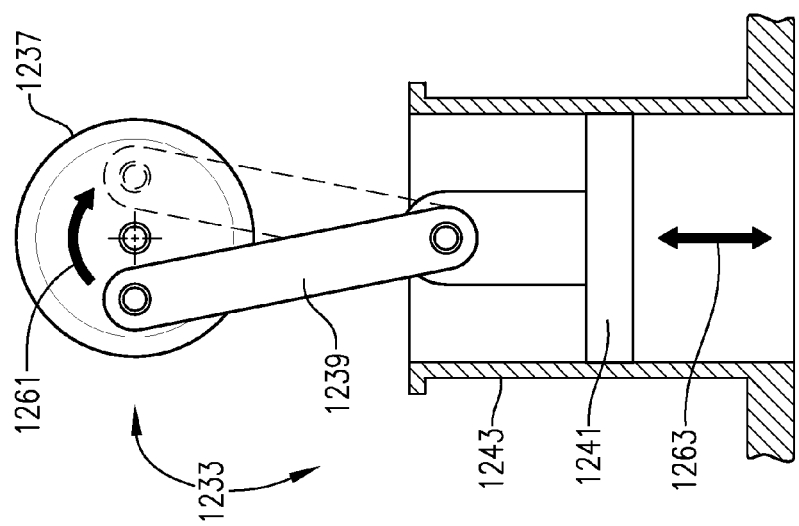
FIG. 13e is a side cut-away view of a rotatable phase shifting device configured according to another embodiment of the present invention, particularly illustrating a drive system that includes a rotating crank member.

Additional embodiments of other rotatable phase shifting devices 1233 and 1235 suitable for use in microwave distribution system 514 of FIG. 6a, are illustrated in FIGS. 13e and 13f, respectively. As shown in the embodiment depicted in FIG. 13e, rotating phase shifting device 1233 can include a rotating crank member 1237 coupled via a securing rod 1239 to a plunger 1241 disposed within a waveguide 1243. As crank member 1237 rotates as indicated by arrow 1261, rod 1239 facilitates a general up-and-down movement of piston or plunger 1241 within waveguide 1243, as indicated by arrow 1263 in FIG. 13e. Another embodiment of a rotating phase shifting device 1235 is depicted in FIG. 13f as including a cam 1245 coupled to a follower rod 1247, which can be integrated with or coupled to a plunger 1241 disposed within waveguide 1243. As cam 1245 rotates, follower rod 1247 moves plunger or piston 1241 in a general up-and-down motion within cylinder 1243, as indicated generally by arrow 1263. Additionally, according to one embodiment, rotating phase shifting device 1235 can further comprise one or more biasing devices 1249 (e.g., one or more springs) for facilitating movement of plunger 1241 within waveguide 1243 in an upward direction.

In addition to being utilized as a rotatable phase shifting device, variable phase short circuit 1230 (or, optionally, rotating phase shifting devices 1233, 1235) can also be configured for use as a tuning device, such as, for example, as an impedance tuner for tuning out or canceling unwanted reflections and/or as a frequency tuner for matching the frequency of the generator to that of the cavity.

Figure 14A:
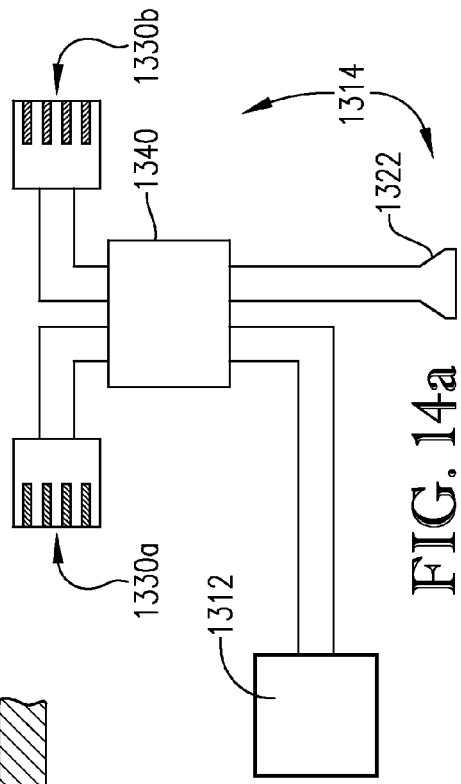
FIG. 14a is a schematic partial side cut-away view of a microwave distribution system utilizing two phase shifting devices for phase shifting and/or impedance tuning.

Turning now to FIG. 14a, one embodiment of a microwave distribution system 1314 utilizing two variable phase short circuits 1330a,b as an impedance tuner for canceling or minimizing reflected power is illustrated. As shown in FIG. 14a, each of variable phase short circuits 1330a,b can be connected to adjacent outlets of a coupler 1340, which can be a short slot hybrid coupler. In operation, each of variable phase short circuits 1330a,b can be individually adjusted to a desired position such that impedance tuner tunes out energy reflected from microwave launcher 1322 back toward generator 1312. According to one embodiment, one or both of variable phase short circuits 1330a,b can be further adjusted as needed during the microwave process in order to accommodate changes in the reflection coefficient of the articles being heated. In one embodiment, the further adjustments can be at least partially carried out using an automatic control system (not shown).

Figure 14B:
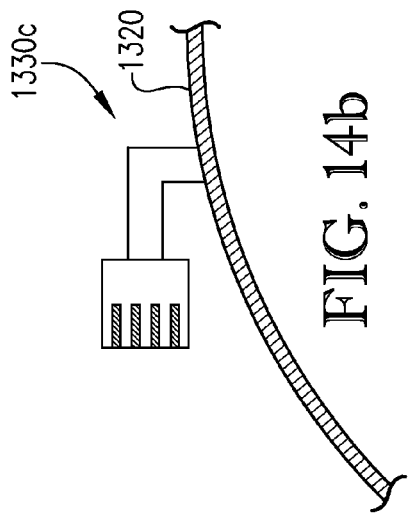
FIG. 14b is a schematic partial side cut-away view of a microwave heating vessel configured according to one embodiment of the present invention, particularly illustrating a phase shifting device coupled to the vessel for use as a frequency tuner.

Variable phase short circuits as described herein can also be utilized as frequency tuners for matching the frequency of the cavity to the frequency of the generator. According to this embodiment, one or more variable phase short circuits, shown as variable phase short circuit 1330c in FIG. 14b, can be directly coupled to individual ports spaced along a resonant microwave chamber 1320. In this embodiment, variable phase short circuit 1330c can be continuously or sporadically rotated and its position can be manually or automatically adjusted depending on changes within microwave chamber 1320 and/or the articles being processed therein (not shown). As a result of this adjustment of variable phase short circuit 1330c, the frequency of microwave energy within the cavity can be more closely matched to the frequency of the generator (not shown).

Figures 15A, 15B:
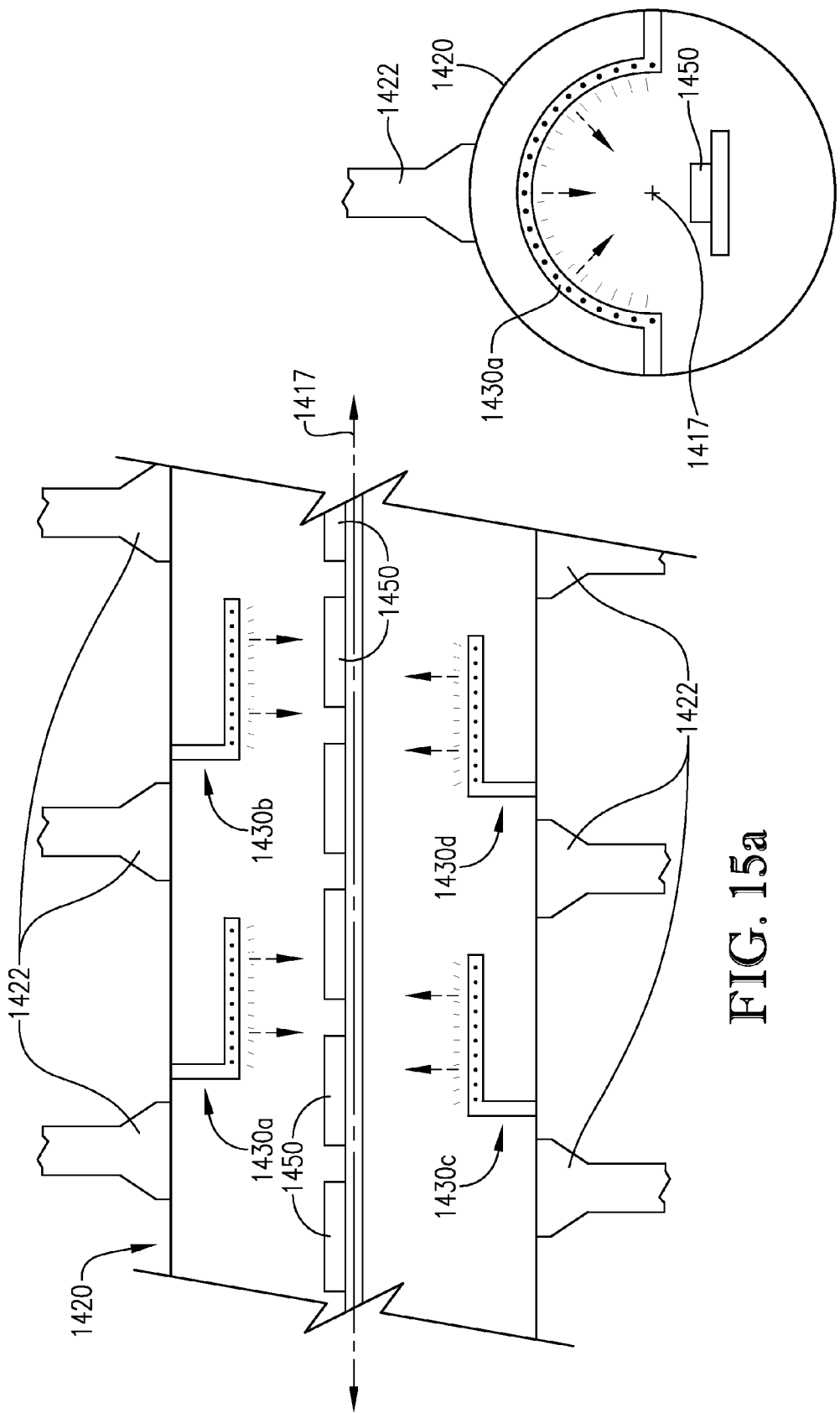
FIG. 15a is a schematic partial side cut-away view of a portion of a microwave heating system, particularly illustrating a thermalization zone including a plurality of fluid jet agitators.
FIG. 15b is an end view of a thermalization zone similar to the one depicted in FIG. 15a, particularly illustrating one embodiment wherein the fluid jet agitator is circumferentially-positioned within the thermalization zone.

Referring again to the microwave heating system 510 shown in FIG. 6a, more thorough and/or more efficient heating of articles 550 passed through microwave chamber 520 may be carried out by, for example, increasing the heat transfer coefficient between the articles and the surrounding fluid medium. One embodiment of a microwave chamber 1420 configured to facilitate quicker and more efficient heating of articles 1450 through changes in the heat transfer coefficient within microwave heating chamber 1420 is illustrated in FIG. 15a. In one embodiment, the heat transfer coefficient within microwave chamber 1420 can be increased, at least in part, by agitating the gaseous or liquid medium within chamber 1420 using one or more agitation devices, such as, for example, one or more fluid jet agitators 1430a-d configured to turbulently discharge one or more fluid jets into the interior of microwave chamber 1420. In one embodiment, the fluid jets discharged into microwave chamber 1420 can be a liquid or a vapor jet and can have a Reynolds number of at least about 4500, at least about 8000, or at least about 10,000.

Structurally, fluid jet agitators 1430a-d can be any device configured to discharge a plurality of jets toward articles 1450 at multiple locations within microwave chamber 1420. In one embodiment, fluid jet agitators 1430 can be axially spaced along the central axis of elongation 1417 of microwave chamber 1420 such that at least a portion of the jets are configured to discharge in a direction generally perpendicular to central axis of elongation 1417. In another embodiment, particularly shown in FIG. 15b, one or more fluid jet agitators 1430a-d can be circumferentially positioned within microwave chamber 1420 such that at least a portion of the jets are directed radially inwardly toward the central axis of elongation 1417 of chamber 1420. Although shown in FIG. 15b as being generally continuous along a portion of the circumference of microwave chamber 1420, it should be understood that fluid jet agitator 1430a may also include a plurality of distinct jets, radially spaced from one another along at least a portion of the circumference of chamber 1420, each positioned to discharge a fluid jet toward central axis of elongation 1417 of chamber 1420.

As shown in FIG. 15a, fluid jet agitators 1430a-d can be positioned along one or more sides of microwave chamber 1420 and can be disposed between (alternately) with one or more microwave launchers 1422. Use of one or more agitators 1430a-d can increase the heat transfer coefficient between the fluid medium within microwave chamber 1420 and articles 1450 by at least about 1 percent, at least about 5 percent, at least about 10 percent, or at least about 15 percent, as compared to the heat transfer coefficient of a quiescent chamber, ceteris paribus. In the same or another embodiment, one or more jets configured and/or operated in a similar manner can be included within one or more other zones of microwave system 10 including thermalization and/or holding zones 12 and/or 20, illustrated previously in FIGS. 1a and 1b.

Referring again to FIGS. 1a and 1b, after being withdrawn from microwave heating zone 16, the heated articles can then optionally be routed to a temperature holding zone 20, wherein the temperature of the articles can be maintained at or above a certain minimum threshold temperature for a specified residence time. As a result of this holding step, the articles removed from holding zone 20 can have a more consistent heating profile and fewer cold spots. In one embodiment, the minimum threshold temperature within holding zone 20 can be the same as the minimum temperature required within microwave heating zone 16 and can be at least about 120° C., at least about 121° C., at least about 122° C. and/or not more than about 130° C., not more than about 128° C., or not more than about 126° C. The average residence time of articles passing through holding zone 20 can be at least about 1 minute, at least about 2 minutes, or at least about 4 minutes and/or not more than about 20 minutes, not more than about 16 minutes, or not more than about 10 minutes. Holding zone 20 can be operated at the same pressure as microwave heating zone 16 and can, in one embodiment, be at least partially defined within a pressurized and/or liquid-filled chamber or vessel.

After exiting holding zone 20, the heated articles of microwave system 10 can subsequently be introduced into a quench zone 22, wherein the heated articles can be quickly cooled via contact with one or more cooled fluids. In one embodiment, quench zone 22 can be configured to cool the articles by at least about 30° C., at least about 40° C., at least about 50° C. and/or not more than about 100° C., not more than about 75° C., or not more than about 50° C. in a time period of at least about 1 minute, at least about 2 minutes, at least about 3 minutes and/or not more than about 10 minutes, not more than about 8 minutes, or not more than about 6 minutes. Any suitable type of fluid can be used as a cooling fluid in quench zone 22, including, for example, a liquid medium such as those described previously with respect to microwave heating zone 16 and/or a gaseous medium.

According to one embodiment generally depicted in FIGS. 1a and 1b, microwave heating system 10 may also include a second pressure adjustment zone 14b disposed downstream of microwave heating zone 16 and/or holding zone 20, when present. Second pressure adjustment zone 14b may be configured and operated in a manner similar to that previously described with respect to first pressure adjustment zone 14a. When present, second pressure adjustment zone 14b can be located downstream of quench zone 22, such that a substantial portion or nearly all of quench zone 22 is operated at an elevated (super atmospheric) pressure similar to the pressure under which microwave heating zone 16 and/or holding zone 20 are operated. In another embodiment, second pressure adjustment zone 14b can be disposed within quench zone 22, such that a portion of quench zone 22 can be operated at a super-atmospheric pressure similar to the pressure of microwave heating zone 16 and/or holding zone 20, while another portion of quench zone 22 can be operated at approximately atmospheric pressure. When removed from quench zone 22, the cooled articles can have a temperature of at least about 20° C., at least about 25° C., at least about 30° C. and/or not more than about 70° C., not more than about 60° C., or not more than about 50° C. Once removed from quench zone 22, the cooled, treated articles can then be removed from microwave heating zone 10 for subsequent storage or use.

In accordance with one embodiment of the present invention, one or more methods for controlling the operation of microwave heating system 10 are provided, for example, to ensure a consistent and continuous exposure to microwave energy for each article or package passing through microwave heating system 10. The major steps of one embodiment of a method 1500 suitable for controlling the operation of microwave system 10 are depicted by individual blocks 1510-1530 in FIG. 16.

Figure 16:
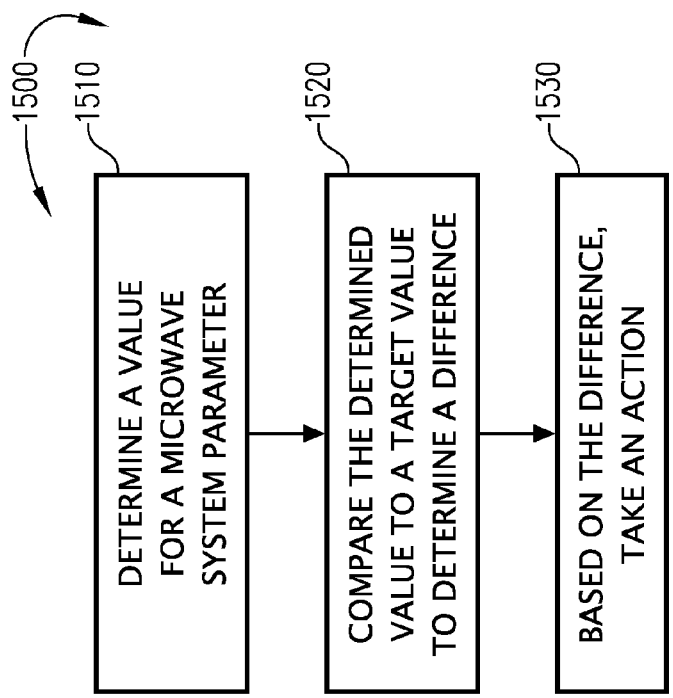
FIG. 16 is a flowchart representing the major steps involved in a method of controlling a microwave system in accordance with one embodiment of the present invention.

As shown in FIG. 16, the first step of control method 1500 is to determine a value for one or more microwave system parameters related to microwave heating zone 16, as represented by block 1510. Examples of microwave system parameters can include, but are not limited to, net power discharged, speed of conveyance system, and temperature and/or flow rate of the water within the microwave heating chamber. Subsequently, as shown by block 1520 in FIG. 16, the resulting determined value for the specific parameter can then be compared to a corresponding target value for the same parameter in order to determine a difference. Based on the difference, one or more actions can be taken to adjust the operation of microwave system 10, as represented by block 1530 in FIG. 16. In one embodiment, the adjustment of microwave heating system 10 can be undertaken when, for example, the magnitude of the difference is at least about 5 percent, at least about 10 percent, or at least about 20 percent of the value of the target value and/or determined value for the specific microwave system parameter. In one embodiment, at least a portion of the above-described method can be carried out using an automatic control system.

In one embodiment, the basic steps of the above-described control method 1500 can be utilized by microwave heating system 10 to ensure safety and/or regulatory compliance of the articles (e.g., food and/or medical fluids or equipment) being heated therein. According to this embodiment, the one or more microwave system parameters may be selected from the group consisting of minimum net power discharged, maximum speed of conveyance system, and minimum temperature and/or minimum flow rate of the water within the microwave heating chamber. In one embodiment, the minimum temperature of the water in the microwave chamber can be at least about 120° C., at least about 121° C., at least about 123° C. and/or not more than about 130° C., not more than about 128° C., or not more than about 126° C., while the minimum flow rate can be at least about 1 gallon per minute (gpm), at least about 5 gpm, or at least about 25 gpm. The maximum speed of the conveyance system, in one embodiment, can be not more than about 15 feet per second (fps), not more than about 12 fps, or not more than about 10 fps and the minimum net power discharged can be at least about 50 kW, at least about 75 kW, or at least about 100 kW. When control method 1500 is utilized to ensure product safety or compliance, the one or more actions taken to adjust the operation of microwave heating system 10 can include, but are not limited to, stopping the conveyance system, turning off one or more generators, removing, isolating, and re-running or disposing of one or more articles exposed to undesirable conditions, and combinations thereof.

In the same or another embodiment, the basic steps of control method 1500 can also be utilized by microwave heating system 10 to ensure quality and consistency amongst the articles (e.g., food and/or medical fluids or equipment) being heated. According to this embodiment, the microwave parameters can include net power discharged, speed of conveyance system, and temperature and/or flow rate of the water within the microwave heating chamber. In one embodiment, the temperature of the water in the microwave chamber can be at least about 121° C., at least about 122° C., at least about 123° C. and/or not more than about 130° C., not more than about 128° C., or not more than about 126° C., while the flow rate can be at least about 15 gallons per minute (gpm), at least about 30 gpm, or at least about 50 gpm. The speed of the conveyance system, in one embodiment, can be controlled to a speed of at least about 5 feet per second (fps), at least about 7 fps, or at least about 10 fps, while the net power discharged can be at least about 75 kW, at least about 100 kW, or at least about 150 kW. When control method 1500 is utilized to ensure product quality or consistency, the one or more actions taken to adjust the operation of microwave heating system 10 can include, but are not limited to, stopping the conveyance system, turning off one or more generators, removing, isolating, and re-running or disposing of one or more articles exposed to undesirable conditions, and combinations thereof.

In order to perform the comparison step 1520 of the method 1500 shown in FIG. 16, one or more of the target values for at least one of the microwave system parameters discussed above can be determined prior to heating the articles in microwave system 10. Determination of the magnitude of these target values may be accomplished by first creating a prescribed heating profile for the specific type of article to be heated using a small-scale microwave system. For example, in one embodiment, one or more articles of a specific type (e.g., particular foodstuffs, medical devices, or medical fluids) are first be loaded into a microwave chamber of a small-scale microwave heating system. In one embodiment, the articles loaded into the small-scale heating chamber can be of a single type such that the resultant prescribed heating determined can be specifically applied to that type of article in a larger-scale heating system. In one embodiment, the article can be a specific type and/or size of packaged food (e.g., an 8-oz MRE package of meat) or can be a packaged medical fluid (e.g., saline) or specific types and/or packages of medical or dental equipment.

Once loaded into the microwave chamber of the small-scale microwave heating system, the article can be heated by introducing microwave energy into the chamber via one or more microwave launchers. During this heating period, which can include multiple heating runs, a prescribed heating profile can be determined for the article being heated. As used herein, the term "prescribed heating profile" refers to a set of target values of a variety of parameters suggested or recommended for use when heating a specific type of article. In addition to including a target values, prescribed heating profiles can also be expressed, at least in part, as a function of time and/or position of the article. In one embodiment, the prescribed heating profile can include at least one target value for one or more microwave system parameters including, but not limited to, net power discharged, sequential distribution of microwave power (i.e., specifics regarding timing, location, and amount of microwave energy discharged), temperature and/or flow rate of the fluid (e.g., water) in the microwave chamber, and/or residence time of the article within the microwave chamber. In addition, the prescribed heating profile can also include target or minimum values for one or more parameters (e.g., temperature, flow rate of fluid, pressure, and article residence time) related to thermalization, holding, and/or quench zones 16, 20, 22 of microwave heating system 10.

Once a prescribed heating profile has been determined, a plurality of that type of article can be loaded into a larger-scale microwave heating system and can then be heated according to the prescribed profile determined with the small-scale microwave system, optionally with the use of an automatic control system. In one embodiment, the small-scale microwave heating system can be a batch or semi-batch system and/or can comprise a liquid-filled microwave chamber having a total internal volume of less than 100 cubic feet, less than 50 cubic feet, or less than 30 cubic feet. In the same or another embodiment, the large-scale microwave system can be a continuous or semi-continuous process at least partially carried out in a pressurized or liquid filled microwave chamber having a total internal volume of at least about 100 cubic feet, at least about 250 cubic feet, or at least about 500 cubic feet. The above-described steps can subsequently be repeated as many times as needed in order to create specific prescribed heating profiles for any number of different articles. Subsequently, target values for one or more parameters described above can be determined and used in the comparison step 1520 of method 1500 shown in FIG. 16. Thereafter and based on the difference, one or more of the actions listed above may be taken to ensure consistent heating of the final product.

One aspect of ensuring consistent heating is ensuring constant and measurable power discharged into the heating zone. In one embodiment, a method for controlling the net power discharged within microwave heating system 10 is provided. As used herein, the term "net power discharged" refers to the difference between the forward and reflected power within a waveguide or launcher. As used herein, the term "forward power" refers to power propagating in an intended direction from the generator to a load, while the term "reflected power" refers to power propagating in a non-intended direction, usually from the load back into a waveguide or launcher and toward the generator.

Figure 17:
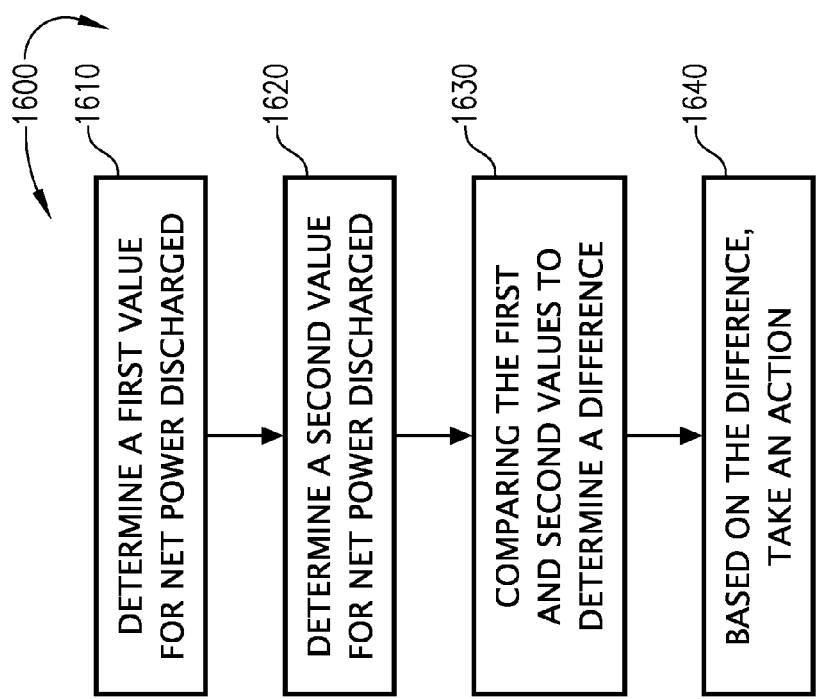
FIG. 17 is a flowchart representing the major steps involved in a method for determining the net power discharged from at least one microwave launcher using two or more pairs of directional couplers.

The major steps of a method 1600 for determining the net power discharged from at least one microwave launcher using two or more pairs of directional couplers are summarized in the flow chart provided in FIG. 17. As represented by blocks 1610 and 1620, a first and second value for net power discharged can be determined using two independent pairs of directional couplers. Each pair of directional couplers can include one coupler for measuring forward power and another for measuring reflected power and one or more devices or systems for calculating the difference to thereby provide respective first and second values for net power discharged. According to one embodiment, at least one of the net power values can be used to adjust or control the output of the microwave generator, while the other can be used as a backup or validation of the other.

Once values have been obtained from each pair of couplers, the first and second values for net power can be compared to determine a difference, as illustrated by block 1630, and, based on the difference, an action can be taken to adjust the operation of the microwave heating system, as depicted by block 1640. In one embodiment, the action can be taken when the difference exceeds a predetermined value, such as, for example, a value that is at least about 1 percent, at least about 2 percent, or at least about 5 percent of the first and/or second net power values determined previously. In one embodiment, action can be taken when the difference is at least about 1 percent, at least about 2 percent, or at least about 3 percent of the lowest of first and second net power values. In another embodiment, action may also be taken if one of first or second net power values falls below a predetermined minimum and/or exceeds a predetermined maximum. Depending, at least in part, on the articles being processed and the difference determined, the action may include, but is not limited to, shutting down a generator or conveyance system, increasing or decreasing generator output, and/or removing, isolating, and disposing or re-running one or more articles that were disposed within the microwave heating chamber when the difference exceeded the predetermined value.

Microwave heating systems of the present invention can be commercial-scale heating systems capable of processing a large volume of articles in a relatively short time. In contrast to conventional retorts and other small-scale systems that utilize microwave energy to heat a plurality of articles, microwave heating systems as described herein can be configured to achieve an overall production rate of at least about 15 packages per minute per convey line, at least about 20 packages per minute per convey line, at least about 25 packages per minute per convey line, or at least about 30 packages per minute per convey line, which far exceeds rates achievable by other microwave systems.

Figure 18:
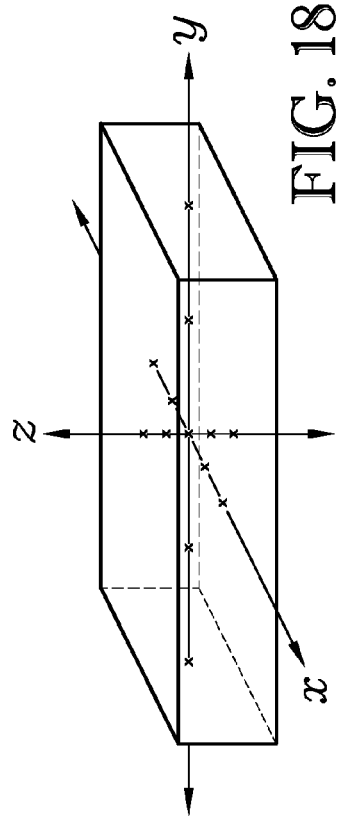
FIG. 18 is an isometric depiction of the location of thermocouples inserted into a test package to determine the minimum temperature of the package for determining the heating profile for an article according to one embodiment of the present invention.

As used herein, the term "packages per minute" refers to the total number of whey gel-filled 8-oz MRE (meals ready to eat) packages able to be processed by a given microwave heating system, according to the following procedure: An 8-oz MRE package filled with whey gel pudding commercially available from Ameriqual Group LLC (Evansville, Ind., USA) is connected to a plurality of temperature probes positioned in the pudding at five equidistant locations spaced along each of the x-, y-, and z-axes, originating from the geometrical center of the package, as shown in FIG. 18. The package is then placed in a microwave heating system being evaluated and is heated until each of the probes registers a temperature above a specified minimum temperature (e.g., 120° C. for sterilization systems). The time required to achieve such a temperature profile, as well as physical and dimensional information about the heating system, can then be used to calculate an overall production rate in packages per minute.

The preferred forms of the invention described above are to be used as illustration only, and should not be used in a limiting sense to interpret the scope of the present invention. Obvious modifications to the exemplary one embodiment, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

The invention claimed is:

1. A variable phase short circuit device for use in a microwave heating system, said device comprising:
 a fixed section defining a first substantially rectangular opening; and
 a rotatable section comprising a housing and a plurality of spaced-apart, substantially parallel plates received in said housing,
 wherein said housing comprises opposite first and second ends, wherein said first end defines a second opening adjacent to said first opening of said fixed section, wherein each of said plates is coupled to said second end of said housing and extends generally toward said first and said second openings, wherein said rotatable section is configured to be rotated relative to said fixed section on an axis of rotation that extends through said first and said second openings.

2. The device of claim 1, wherein said housing has a length ($L_1$), a width ($W_1$) and a depth ($D_1$), wherein said variable phase short circuit is configured to pass microwave energy having a wavelength ($\lambda$) from said first opening to said housing, wherein at least one of $W_1$ and $D_1$ is greater than $0.5\lambda$.

3. The device of claim 2, wherein both $W_1$ and $D_1$ are less than $1\lambda$.

4. The device of claim 2, wherein the ratio of $W_1:D_1$ is less than 1.5:1.

5. The device of claim 1, wherein said variable phase short circuit is configured to pass microwave energy having a wavelength ($\lambda$) from said first opening to said housing, wherein adjacent plates within said housing are spaced apart by no more than $0.1\lambda$.

6. The device of claim 1, wherein each of said plates presents a distal end having a first surface area facing toward said first and second openings, wherein said second end of said housing defines an exposed inner surface area located between said plates and facing toward said first and second openings, wherein the ratio of the sum of the first surface areas of the distal ends of said plates to the exposed surface area of said second end of said housing is at least 0.5:1 and not more than 2:1.

7. The device of claim 1, wherein said variable phase short circuit is configured to pass microwave energy having a wavelength ($\lambda$) from said first opening into said housing, wherein said plates extend toward said first side for a distance of at least $0.25\lambda$.

8. The device of claim 1, wherein said first opening has a length ($L_2$), a width ($W_2$) and a depth ($D_2$), wherein the ratio of $W_2:D_2$ is greater than 1.25:1.

9. The device of claim 8, wherein said housing has a length ($L_1$), a width ($W_1$), and a depth ($D_1$), wherein $W_1$ and $W_2$ are substantially equal.

10. The device of claim 9, wherein the ratio of $W_1:D_1$ is less than 1.2:1.

11. The device of claim 1, further comprising a microwave choke disposed proximate said first and second openings and configured to inhibit leakage of microwave energy from between said fixed and rotatable sections.

12. The device of claim 1, further comprising an actuator for rotating said rotatable section at a speed of at least 50 revolutions per minute (rpm).

13. The device of claim 1, wherein said rotatable section is configured to be adjusted manually via rotation to a desired position.

14. The device of claim 1, wherein said variable phase short circuit is configured to be connected to a coupler and utilized as a phase shifting device in a microwave system for heating a plurality of articles.

* * * * *